United States Patent
Zahid et al.

(10) Patent No.: US 10,657,642 B2
(45) Date of Patent: May 19, 2020

(54) SYSTEM, METHOD AND COMPUTER-ACCESSIBLE MEDIUM FOR THE DETERMINATION OF ACCELERATED BRAIN ATROPHY AND AN OPTIMAL DRAINAGE SITE FOR A SUBDURAL HEMATOMA USING COMPUTED TOMOGRAPHY

(71) Applicant: New York University, New York, NY (US)

(72) Inventors: Abdullah Bin Zahid, Minneapolis, MN (US); Henry Rusinek, Great Neck, NY (US); Artem Mikheev, New York, NY (US); Uzma Samadani, Minneapolis, MN (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/737,855

(22) PCT Filed: Jun. 20, 2016

(86) PCT No.: PCT/US2016/038408
§ 371 (c)(1),
(2) Date: Dec. 19, 2017

(87) PCT Pub. No.: WO2016/205811
PCT Pub. Date: Dec. 22, 2016

(65) Prior Publication Data
US 2019/0012783 A1   Jan. 10, 2019

Related U.S. Application Data

(60) Provisional application No. 62/182,132, filed on Jun. 19, 2015.

(51) Int. Cl.
*G06T 7/00* (2017.01)
*A61B 6/00* (2006.01)
(Continued)

(52) U.S. Cl.
CPC ............ *G06T 7/0012* (2013.01); *A61B 6/032* (2013.01); *A61B 6/501* (2013.01); *A61B 6/5217* (2013.01);
(Continued)

(58) Field of Classification Search
None
See application file for complete search history.

(56) References Cited

U.S. PATENT DOCUMENTS 7,641,343 B1   1/2010   Motamedi et al.
2004/0092814 A1   5/2004   Hsieh et al.
(Continued)

OTHER PUBLICATIONS

Calculation of brain atrophy using computed tomography and a new atrophy measurement tool. Zahid et al. Mar. 2015.*
(Continued)

*Primary Examiner* — Delomia L Gilliard
(74) *Attorney, Agent, or Firm* — Ballard Spahr LLP

(57) ABSTRACT

To that end, in order to overcome some of the deficiencies presented herein above, an exemplary system, method and computer-accessible medium for determining an attribute(s) of a brain of a patient, can include, for example, receiving information obtained from a computed tomography ("CT") scan(s) of a portion(s) of the brain, generating a CT image(s) that can be based on the information, and determining the attribute(s) of the brain based on the CT image(s) by segmenting an intracranial space (ICS) in the CT image(s). The attribute(s) can include a presence or absence of Alzheimer's disease, total volume of the ICS, brain, CSF or a lesion or the volumes of ICS, brain, CSF or lesion(s)
(Continued)

expressed as a percentage of other volume(s). The aforementioned areas can be segmented using a combination of thresholding, morphological erosions, morphological dilations, manual segmentation or semi-automatic segmentation techniques, all of which can be parallel procedures. These attributes can be further used to determine treatment, for example, optimizing the location of the twist drill craniotomy to drain hematoma in subdural hematoma.

28 Claims, 13 Drawing Sheets

(51) Int. Cl.
| | |
|---|---|
| A61B 6/03 | (2006.01) |
| G06T 7/136 | (2017.01) |
| G06T 7/155 | (2017.01) |
| G06T 7/11 | (2017.01) |
| G06T 7/70 | (2017.01) |
| G01R 33/48 | (2006.01) |
| A61B 5/055 | (2006.01) |
| A61B 5/00 | (2006.01) |

(52) U.S. Cl.
CPC .......... *A61B 6/5247* (2013.01); *A61B 6/5252* (2013.01); *G06T 7/11* (2017.01); *G06T 7/136* (2017.01); *G06T 7/155* (2017.01); *G06T 7/70* (2017.01); *A61B 5/055* (2013.01); *A61B 5/4088* (2013.01); *A61B 2576/026* (2013.01); *G01R 33/4812* (2013.01); *G06T 2207/10081* (2013.01); *G06T 2207/30016* (2013.01); *G06T 2207/30096* (2013.01)

(56) References Cited

U.S. PATENT DOCUMENTS

| | | | | |
|---|---|---|---|---|
| 2012/0330196 | A1* | 12/2012 | Nita | A61N 7/022 601/2 |
| 2014/0270052 | A1* | 9/2014 | Vestevich | A61B 6/501 378/4 |

OTHER PUBLICATIONS

Mori et al., Surgical Treatment of Chronic Subdural Hematoma in 500 Consecutive Cases: Clinical Characteristics, Surgical Outcome, Complications, and Recurrence Rate, Neurol. Med. Chir. (Tokyo), vol. 41, 2001, pp. 371-381.
Nakaguchi et al., Relationship between drainage catheter location and postoperative recurrence of chronic subdural hematoma after burr-hole irrigation and closed-system drainage, J. Neurosurg. vol. 93, 2000, pp. 791-795.
Nayil et al., Subdural Hematomas: An Analysis of 1181 Kashmiri Patients, World Neurosurgery, vol. 77(1), Jan. 2012, pp. 103-110.
Neal et al., The Subdural Evacuation Port System: Outcomes from a single institution experience and predictors of success, Clinical Neurology and Neurosurgery, vol. 115, 2013, pp. 658-664.
Neils et al., Recurrence-Free Chronic Subdural Hematomas: A Retrospective Analysis of the Instillation of Tissue Plasminogen Activator in Addition to Twist Drill or Burr Hole Drainage in the Treatment of Chronic Subdural Hematomas, World Neurosurgery, vol. 78, 2012, pp. 145-149.
Nugent et al., Automated Subcortical Segmentation using FIRST: Test-Retest reliability, Inter-scanner reliability, and Comparison to Manual Segmentation, Human Brain Mapping, vol. 34(9), Sep. 2013, pp. 2313-2329.
Ohba et al., The risk factors for recurrence of chronic subdural hematoma, Neurosurgical Review, vol. 36, 2013, pp. 145-150.
Resnick et al., Longitudinal Magnetic Resonance Imaging Studies of Older Adults: A Shrinking Brain, The Journal of Neuroscience, vol. 23(8), 2003, pp. 3295-3301.
Rusinek et al., Atrophy rate in medial temporal lobe during progression of Alzheimer disease, Neurology, vol. 63, 2004, pp. 2354-2359.
Safain, M.D. et al., A single center's experience with the bedside subdural evacuating port system: a useful alternative to traditional methods for chronic subdural hematoma evacuation, J. Neurosurg. vol. 118, 2013, pp. 694-700.
Santarius et al., The management of primary chronic subdural haematoma: a questionnaire survey of practice in the United Kingdom and the Republic of Ireland, British Journal of Neurosurgery, vol. 22(4), Aug. 2008, pp. 529-534.
Sarnvivad M.D. et al., Chronic Subdural Hematoma: Drainage vs. No Drainage, Journal of the Medical Association of Thailand, vol. 94(11), 2011, pp. 1352-1356.
Scahill et al., A Longitudinal Study of Brain Volume Changes in Normal Aging Using Serial Registered Magnetic Resonance Imaging, Arch. Neurol., vol. 60(7), 2003, pp. 989-994.
Schuff et al., MRI of Hippocampal volume loss in early Alzheimer's disease in relation to ApoE genotype and biomarkers, Brain, vol. 132, 2009, pp. 1067-1077.
Shimizu et al., Intraoperative Ultrasonography during Drainage for Chronic Subdural Hematomas: A Technique to Release Isolated Deep-seated Hematomas—Technical Note, Neurologia medico-chirurgica, vol. 55, 2015, pp. 761-765.
Swearer et al., Rate of Progression in Familial Alzheimer's Disease, Journal of Geriatr Psychiatry Neurol., vol. 9, 1996, pp. 22-25.
Taber et al., Blast-Related Traumatic Brain Injury: What is Known? Journal of Neuropsychiatry Clin. Neurosci., vol. 18(2), 2006, pp. 141-145.
Tahsim-Oglou et al., Factors predicting recurrence of chronic subdural haematoma: the influence of intraoperative irrigation and low-molecular-weight heparin thromboprophylaxis, Acta. Neurochir., vol. 154, 2012, pp. 1063-1068.
Thompson et al., Dynamics of Gray Matter Loss in Alzheimer's Disease, The Journal of Neuroscience, vol. 23(3), Feb. 2003, pp. 994-1005.
Wang et al., MR image-based measurement of rates of change in volumes of brain structures. Part II: Application to a study of Alzheimer's disease and normal aging, Magnetic Resonance Imaging, vol. 20, 2002, pp. 41-48.
Weigel et al., Specific Pattern of Growth Factor Distribution in Chronic Subdural Hematoma (CSH): Evidence for an Angiogenic Disease, Acta. Neurochir (Wien), vol. 143, 2001, pp. 811-819.
Weigel et al., Outcome of contemporary surgery for chronic subdural haematoma: evidence based review, Journal of Neurology, Neurosurgery & Psychiatry, vol. 74, 2003, pp. 937-943.
Xi et al., Mechanisms of brain injury after intracerebral haemorrhage, The Lancet Neurology, vol. 5, Jan. 2006, pp. 53-63.
Yang et al., Cerebral atrophy is associated with development of chronic subdural haematoma, Brain Inj., vol. 26, 2012, pp. 1731-1736.
Zahid et al. "Calculation of brain atrophy using computed tomograph and a new atrophy measurement tool," In: Proceedings of SPIE, vol. 9413, Medical Imaging 2015.
International Search Report for International Application No. PCT/US2016/038408 dated Oct. 28, 2016.
International Written Opinion for International Application No. PCT/US2016/038408 dated Oct. 28, 2016.
Almenawer et al., Chronic Subdural Hematoma Management: A Systematic Review and Meta-analysis of 34,829 Patients: Annals of Surgery, vol. 259 (3), Mar. 2014, pp. 449-457.
Altamura et al., Iron Toxicity in Diseases of Aging: Alzheimer's Disease, Parkinson's Disease and Atherosclerosis: Journal of Alzheimer's Disease, vol. 16, 2009, pp. 879-895.
Balser et al., Evolving management of symptomatic chronic subdural hematoma: experience of a single institution and review of the literature, Neurological Research, vol. 35(3), 2013, pp. 233-242.

(56) References Cited

OTHER PUBLICATIONS

Balser et al., Actual and projected incidence rates for chronic subdural hematomas in the United States Veterans Administration and civilian populations, J. Neurosurg. vol. 123(5), Nov. 2015, pp. 1-14.

Berhouma et al., The minimally invasive endoscopic management of septated chronic subdural hematomas: surgical technique, Acta Neurochir., vol. 156, 2014, pp. 2359-2362.

Bin Zahid et al., Calculation of brain atrophy using computed tomography and a new atrophy measurement tool, Proc. SPIE 9413, Medical Imaging 2015: Image Processing, 2015, pp. 94132S-1-94132S-9.

Bohnert et al., Veteran Status and Alcohol Use in Men in the United States, Military Medicine, vol. 177, 2012, pp. 198-203.

Borger et al., Chronic subdural haematoma in elderly patients: a retrospective analysis of 322 patients between the ages of 65-94 years, Acta. Neurochir, vol. 154, 2012, pp. 1549-1554.

Bos et al., Calcification in Major Vessel Beds Relates to Vascular Brain Disease, Arterioscler Thromb Vasc Biol, vol. 31(10), 2011, pp. 2331-2337.

Bray et al., 2008 Department of Defense Survey of Health Related Behaviors Among Active Duty Military Personnel, RTI International 2009, pp. 1-678.

Cenic et al., Management of Chronic Subdural Hematoma: A National Survey and Literature Review, Can. J. Neurol. Sci., vol. 32, 2005, pp. 501-506.

Chan et al., Change in rates of cerebral atrophy over time in early-onset Alzheimer's disease: longitudinal MRI study, The Lancet, vol. 362, Oct. 2003, pp. 1121-1122.

Cole et al., Prediction of Brain Age Suggests Accelerated Atrophy after Traumatic Brain Injury, Ann. Neurol., vol. 77, 2015, pp. 571-581.

De Leon et al., Early Marker for Alzheimer's Disease: The Atrophic Hippocampus, Lancet, vol. 2, 1989, pp. 672-673.

Dekaban et al., Changes in Brain Weights During the Span of Human Life: Relation of Brain Weights to Body Heights and Body Weights, Ann Neurol., vol. 4(4), 1978, pp. 345-356.

Ducruet et al., The surgical management of chronic subdural hematoma, Neurosurgical Review, vol. 35, 2012, pp. 155-169.

Dumont et al., Chronic Subdural Hematoma: A Sentinel Health Event, World Neurosurgery, vol. 80, 2013, pp. 889-892.

Duning et al., Dehydration confounds the assessment of brain atrophy, Neurology, vol. 64, 2005, pp. 548-550.

Filippini, Epidemiology of primary central nervous system tumors, Handbook of Clinical Neurology, vol. 104(3), 2012, pp. 3-22.

Frank et al., Biological markers for therapeutic trials in Alzheimer's disease Proceedings of the biological markers working group; NIA initiative on neuroimaging in Alzheimer's disease, Neurobiology of Aging, vol. 24, 2003, pp. 521-536.

Frati et al., Inflammation markers and risk factors for recurrence in 35 patients with a posttraumatic chronic subdural hematoma: a prospective study, J. Neurosurg., vol. 100, 2004, pp. 24-32.

Frontera et al., Trend in Outcome and Financial Impact of Subdural Hemorrhage, Neurocrit Care, vol. 14, 2011, pp. 260-266.

Ganguli et al., Who Wants a Free Brain Scan? Assessing and Correcting for Recruitment Biases in a Population-Based sMRI Pilot Study, Brain Imaging Behavior, vol. 9(2), Jun. 2015, pp. 204-212.

Gavrilovic et al., Brain metastases: epidemiology and pathophysiology, Journal of Neuro-Oncology, vol. 75, 2005, pp. 5-14.

Gökmen et al., Randomized Comparative Study of Burr-hole Craniostomy Versus Twist Drill Craniostomy; Surgical Management of Unilateral Hemispheric Chronic Subdural Hematomas, vol. 69, 2008, pp. 129-133.

Göksu et al., Spontaneous resolution of a large chronic subdural hematoma: a case report and review of the literature, ulus Travma Acil Cerrahi Derg = Turkish Journal of Trauma & Emergency Surgery: TJTES, vol. 15(1), 2009, pp. 95-98.

Gelabert-Gonzalez et al., Chronic subdural haematoma: surgical treatment and outcome in 1000 cases, Clinical Neurology and Neurosurgery, vol. 107, 2005, pp. 223-229.

Gunter et al., Methodological Considerations for Measuring Rates of Brain Atrophy, J. Magn. Reson. Imaging, vol. 18(1), Jul. 2003, pp. 16-24.

Hamilton et al., Chronic Subdural Hematoma: The Role of Craniotomy Reevaluated, Neurosurgery, vol. 33(1), 1993, pp. 67-72.

Hoge et al., Mild Traumatic Brain Injury in U.S. Soldiers Returning from Iraq, The New England Journal of Medicine, vol. 358(5), Jan. 2008, pp. 453-463.

Hua et al., Brain Injury After Intracerebral Hemorrhage, The Role of Thrombin and Iron, Stroke, vol. 38, 2007, pp. 759-762.

Ito et al., Fibrin and Fibrinogen Degradation Products in Chronic Subdural Hematoma, Neurologia medico-chirurgica, vol. 15, 1975, pp. 51-55.

Jack CR, Jr. et al., Atrophy Rates Accelerate in Amnestic Mild Cognitive Impairment, Neurology, vol. 70, 2008, pp. 1740-1752.

Jack CR, Jr. et al., Comparison of Different MRI Brain Atrophy Rate Measures with Clinical Disease Progression in AD, Neurology, vol. 62(4), Feb. 2004, pp. 591-600.

Juković et al., Complete spontaneous resolution of compressive chronic subdural hematoma in a patient with liver failure, Medicinski Glasnik, vol. 9(2), Aug. 2012, pp. 417-420.

Kempton et al., Dehydration Affects Brian Structure and Function in Healthy Adolescents, Human Brain Mapping, vol. 32, 2011, pp. 71-79.

Kirsch et al., Serial Susceptibility Weighted MRI measures brain iron and microbleeds in dementia, J. Alzheimers Dis., vol. 17(3), 2009, pp. 599-609.

Kolias et al., Surgical management of chronic subdural hematomas: in need of better evidence, Acta Neurochirurgica, vol. 155, 2013, pp. 183-184.

Kudo et al., Chronic Subdural Hematoma in Elderly People: Present Status on Awaji Island and Epidemiological Prospect, Neruol. Med. Chir., vol. 32, 1992, pp. 207-209.

Lee, The pathogenesis and clinical significance of traumatic subdural hygroma, Brain Injury, vol. 12(7), 1998, pp. 595-603.

Lega et al., Choosing the best operation for chronic subdural hematoma: a decision analysis, J. Neurosurg. vol. 113, 2010, pp. 615-621.

Leroy et al., Predictors of functional outcomes and recurrence of chronic subdural hematomas, Journal of Clinical Neuroscience, vol. 22, 2015, pp. 1895-1900.

Leung et al., Cerebral atrophy in mild cognitive impairment and Alzheimer disease, Neurology, vol. 80, Feb. 2013, pp. 648-654.

Liu et al., Chronic subdural hematoma: a systematic review and meta-analysis of surgical procedures, J. Neurosurg., vol. 121, 2014, pp. 665-673.

Markwalder M.D., Chronic subdural hematomas: a review, J. Neurosurg. vol. 54, 1981, pp. 637-645.

McKhann et al., The diagnosis of dementia due to Alzheimer's disease: Recommendations from the National Institute of Aging-Alzheimer's Association workgroups on diagnostics guidelines from Alzheimer's disease, Alzheimers Dement., vol. 7(3), May 2011, pp. 263-269.

Mellergard et al., Operations and Re-Operations for Chronic Subdural Haematomas During a 25-Year Period in a Well Defined Population, Acta Neurochir. (Wein), vol. 138, 1996, pp. 708-713.

Mikheev et al., Fully Automatic Segmentation of the Brain From T1-Weighted MRI Using Bridge Burner Algorithm, J. Magn. Reson. Imaging., vol. 27(6), Jun. 2008, pp. 1-17.

Mills et al., Mechanisms of Brain Iron Transport: Insight into Neurodegeneration and CNS Disorders, Future Md. Chem., vol. 2(1), Jan. 2010, pp. 1-22.

Miranda et al., Chronic subdural hematoma in the elderly: not a benign disease, J. Neurosurg. vol. 114, 2011, pp. 72-76.

Beer, Ferdinand et al., "Vector Mechanics for Engineers, Statics and Dynamics," 9th Edition, McGraw Hill Higher Education, pp. 1-36, 2007.

De Jesus, Orlando et al., "Chronic and Subacute Subdural Hematoma in the Adult Population. The Puerto Rico Experience," RKSJ, vol. 17, No. 3, pp. 227-233, Sep. 1998.

(56) References Cited

OTHER PUBLICATIONS

Ito, Haruhide et al., "Fibrin and Fibrinogen Degradation Products in Chronic Subdural Hematoma," Neurologia Medico-chirurgica, pp. 51-55, 1975.
Suzuki, K. et al., "Increased Concentration of Vascular Endothelial Growth factor (VEGF) in Chronic Subdural Hematoma," J. Trauma, vol. 46, pp. 532-533, 1999.
Kenning, Tyler J. et al., "Analysis of the subdural Evacuating port System for the Treatment of Subacute and Chronic Subdural Hematomas," J. Neurosurg, vol. 113, pp. 1004-1010, 2010.
Nagata, K. et al., "Studies on the Operative factors Affecting the reduction of Chronic subdural Hemtoma, with Special reference to the residual air in the hematoma Cavity," No Shinke Geka, vol. 17, No. 1, pp. 15-20, Jan. 1989.
Courchesne, Eric et al., "Normal Brain Development and Aging: Quantitative Analysis at in Vivo MR Imaging in Healthy Volunteer," Radiology, vol. 216, pp. 672-682, 2000.

\* cited by examiner

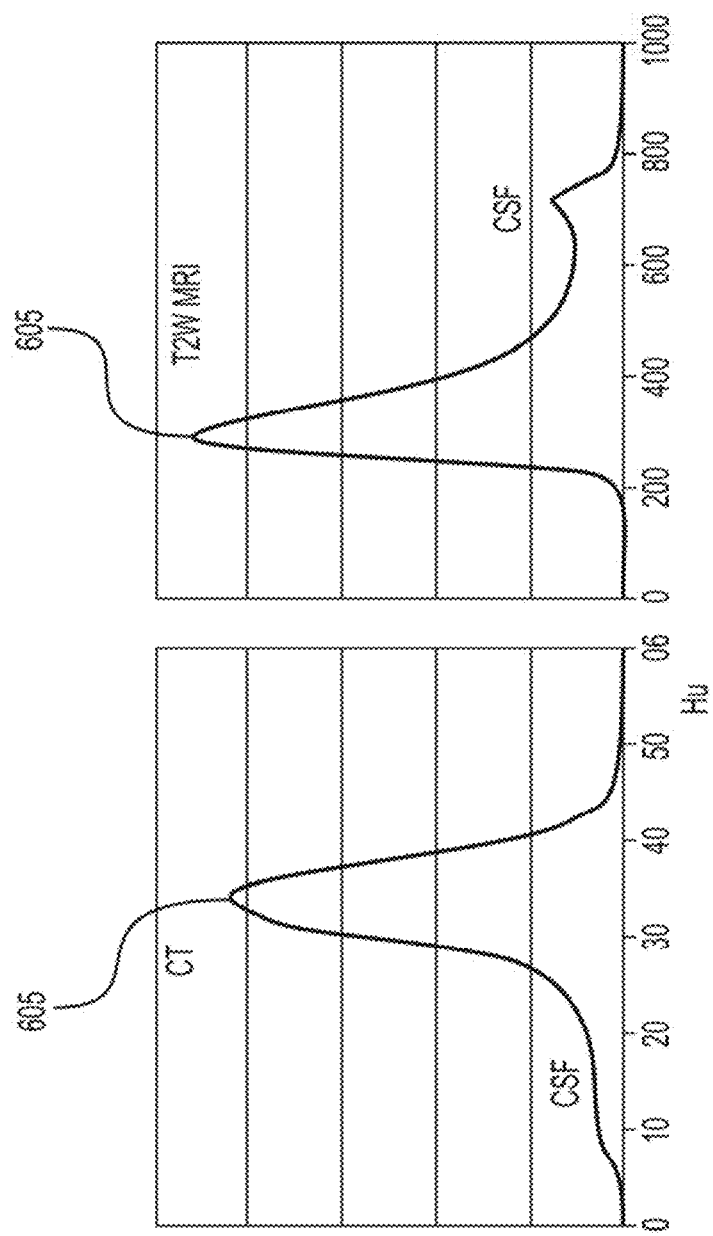

SYSTEM, METHOD AND COMPUTER-ACCESSIBLE MEDIUM FOR THE DETERMINATION OF ACCELERATED BRAIN ATROPHY AND AN OPTIMAL DRAINAGE SITE FOR A SUBDURAL HEMATOMA USING COMPUTED TOMOGRAPHY

CROSS-REFERENCE TO RELATED APPLICATION(S)

This application relates to and claims the benefit and priority from International Patent Application No. PCT/US2016/038408 filed on Jun. 20, 2016 that published as International Patent Publication No. WO 2016/205811 on Dec. 22, 2016, which claims the benefit and priority from U.S. Patent Application Ser. No. 62/182,132, filed on Jun. 19, 2015, the entire disclosures of which is are incorporated herein by reference.

FIELD OF THE DISCLOSURE

The present disclosure relates generally to computed tomography ("CT"), and more specifically, to exemplary embodiments of an exemplary system, method and computer-accessible medium for the determination of accelerated brain atrophy and radiodensity using serial computed tomography.

BACKGROUND INFORMATION

In order to test therapeutics for Alzheimer's disease ("AD"), it can be important to first be able to assess disease progression. Underlying clinical progression in AD can include neuropathologic changes that follow a pattern of spreading atrophy throughout the brain, starting in the medial temporal lobe. (See, e.g., Reference 1). With the prospect of disease-modifying therapies, early detection and accurate monitoring of such progression can be an important goal. The most frequently studied in vivo marker for AD progression is the brain atrophy rate derived from serial magnetic resonance imaging ("MRI"). Numerous cross-sectional studies have reported the average brain volume loss in AD to be several times greater than approximately 0.5%/year rate in non-demented elderly. (See, e.g., References 2-5). Accelerated within-subject brain volume loss has also been reported. (See, e.g., Reference 6).

Serial imaging facilitates specific assessment of progression, as the patient serves as his or her own reference baseline. In addition to AD, assessments of brain atrophy rates can also be of importance in hydrocephalus, traumatic injury and multiple sclerosis, since they can help gauge brain insult and its response to treatment. (See, e.g., References 7-9).

As early as in the 1980s, serial CT imaging studies showed abnormally large ventricular and sulcal enlargement in AD patients. Later, after the advent of MRI, the emphasis was placed on calculation of atrophy using MRI, given the better soft tissue Whereas there are virtually no published studies of brain atrophy in CT for Alzheimer's disease, modern CT has many advantages over MRI, including: (i) lower cost of both the imaging system and patient exam, (e.g., CT is less than about ½ of the cost of MRI), (ii) 100 times faster speed of acquisition (e.g., fewer motion artifacts), (iii) availability, (iv) spatial resolution, and (v) fewer limitations related to claustrophobia and the presence of ferromagnetic material (e.g., metal) in the body. The disadvantages of CT include lower contrast/noise, and exposure of the patient to ionized radiation. While radiation exposure can be of concern, the risk/benefit equation can be age- and organ-dependent, favoring the use of CT to study brain atrophy in the elderly.

Chronic subdural hematoma ("cSDH") has become increasingly prevalent in the aging civilian and veteran population, and is projected to become the most common indication for an adult cranial procedure in the United States by 2030. (See, e.g., Reference 25). It is tenfold more common among Veterans Administration patients than civilians (see, e.g., Reference 25), and has a high mortality in the veteran population, with about 32% of afflicted patients between ages 65 and 96 dying within 1 year of diagnosis. (See, e.g., Reference 26). cSDH has a high recurrence rate (see, e.g., References 27, 28, 29, and 30), and patients often need prolonged hospitalization and rehabilitation. (See, e.g., References 31 and 32).

cSDH has traditionally been treated by surgical drainage via craniotomy or burr hole craniostomy in the operating room, or more recently, by twist drill craniostomy at the patient bedside. The purpose of drainage for cSDH is not only to relieve immediate mass effect on the brain, but also to remove toxic blood break-down products. Iron toxicity is a potential effector of cognitive outcome. (See, e.g., References 33, 34, 39, and 36). Increased extent of drainage of cSDH correlates with improved clinical outcomes, such as increased survival (see, e.g., Reference 37), reduced recurrence (see, e.g., References 38 and 39) and better functional outcome. (See, e.g., Reference 40).

Meta-analysis of 830 publications comparing craniotomy, burr holes and twist-drill for cSDH, found burr hole craniostomy to have the best outcome of the three treatment options by a narrow margin. After correction for selection bias, craniotomies resulted in the most deaths, burr holes resulted in the most nonfatal complications, and twist drills had the highest recurrence with the least proportion cured. (See, e.g., Reference 41). The increased recurrence of hematomas with twist drills has been found in several other studies (see, e.g., References 42, 43, 44 and 45) and it is hypothesized to be at least partially due to suboptimal drain placement. The current standard of care for twist drill craniostomy drainage of cSDH is that surgeon approximates optimal placement of the drain site with attention to the density, thickness and shape of the cSDH based on viewing of a series of two-dimensional CT More optimal placement of bedside twist drill craniostomies could potentially improve drainage, shorten hospitalization, reduce recurrence and improve cognitive outcomes. Since twist drills are performed at the bedside, with decreased anesthesia, their improved efficacy enable decreased perioperative anesthetic complications.

Thus, it may be beneficial to provide an exemplary system, method and computer-accessible medium for the determination of accelerated brain atrophy, radiodensity and optimal drainage site using CT, which can overcome at least some of the problems presented herein above.

SUMMARY OF EXEMPLARY EMBODIMENTS

To that end, in order to overcome some of the deficiencies presented herein above, an exemplary system, method and computer-accessible medium for determining an attribute(s) of a brain of a patient, can include, for example, receiving information obtained from a computed tomography ("CT") scan(s) of a portion(s) of the brain, generating a CT image(s) that can be based on the information, and determining the attribute(s) of the brain based on the CT image(s) by segmenting an intracranial space (ICS) or the lesion of interest (e.g. hematoma) in the CT image(s). The attribute(s) can include a presence or absence of Alzheimer's disease, and can also include a total volume of the brain, brain volume as a percent of cranial cavity or volume of the lesion, or attribute(s) of the lesion (e.g. centroid, most dependent part). The ICS can be segmented by performing thresholding CT image, which can be a parallel procedure. The procedure can be performed by selecting a plurality of voxels in the second imaging information that have a particular CT attenuation range, where the range can be from about −500 Hounsfield units (HU) to about +125 HU.

In some exemplary embodiments of the present disclosure, small soft tissue structures that link the brain to a face of the patient can be substantially eliminate from the image(s). The small soft tissue structures can be eliminated using a morphological erosion procedure. A default radius of the morphological erosion procedure can be about 5 millimeters. The small soft tissue structures can include nerves and blood vessels. The morphological erosions thus performed may result in the loss of ICS volume, which can be recovered using morphological dilations. The ICS volume can thus be determined based on CT image(s). The ICS can be decomposed into at least two distinct portions, which can be cerebral spinal fluid ("CSF") volume of the patient and the brain. The ICS can be by separating the CSF volume from the brain by selecting all ICS voxels having an value within a fluid range. The fluid range can be less than about 16 Hounsfield units. The attenuation values for the fluid range can be determined from a multimodality co-registration procedure, which can be based on CT and $T_2$-weighted magnetic resonance imaging. The attenuation values can also be determined by visually inspecting CT scan and changing the upper and lower thresholds till satisfactory results are obtained.

According to a further exemplary embodiment of the present disclosure, exemplary system, method and computer-accessible medium can be provided for determining a drainage site of a lesion(s) in a patient. For example, it is possible to receive a location of the lesion in a CT image(s), determine an attribute(s) of the lesion(s) based on the location, and ascertain the drainage site based on the attribute(s). The attribute(s) can include (i) a centroid, (ii) a density weighted centroid, (iii) a major axis, (iv) a minor axis, (v) a topmost part of the lesion or (vi) a most dependent part of the subdural hematoma. The attribute(s) can be determined based on at least one of (i) a shape of the lesion(s), (ii) a type of the lesion(s) or (iii) a septation of the lesion(s). The lesion(s) can be (i) a hematoma, (ii) a subdural hygroma, (iii) an abscess on a surface of a brain of the patient or (iv) a solid that has aspirated through a drain of the patient. The drainage site can be a point on a scale that can be determined based on the attribute(s). The location of the lesion(s) in the CT image can be automatically determined by a computer and/or can be identified by a person(s).

In certain exemplary embodiments of the present disclosure, information obtained from a CT scan(s) of the lesion(s) can be received, and a CT image(s) can be generated based on the information. The drainage site can be an optimal drainage site.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 6B is an exemplary graph illustrating the histogram of the intracranial space of a computed tomography scan image according to an exemplary embodiment of the present disclosure;

FIG. 6C is an exemplary graph illustrating the histogram of the intracranial space of T2 magnetic resonance imaging data according to an exemplary embodiment of the present disclosure;

DETAILED DESCRIPTION OF EXEMPLARY EMBODIMENTS

Figure 1:
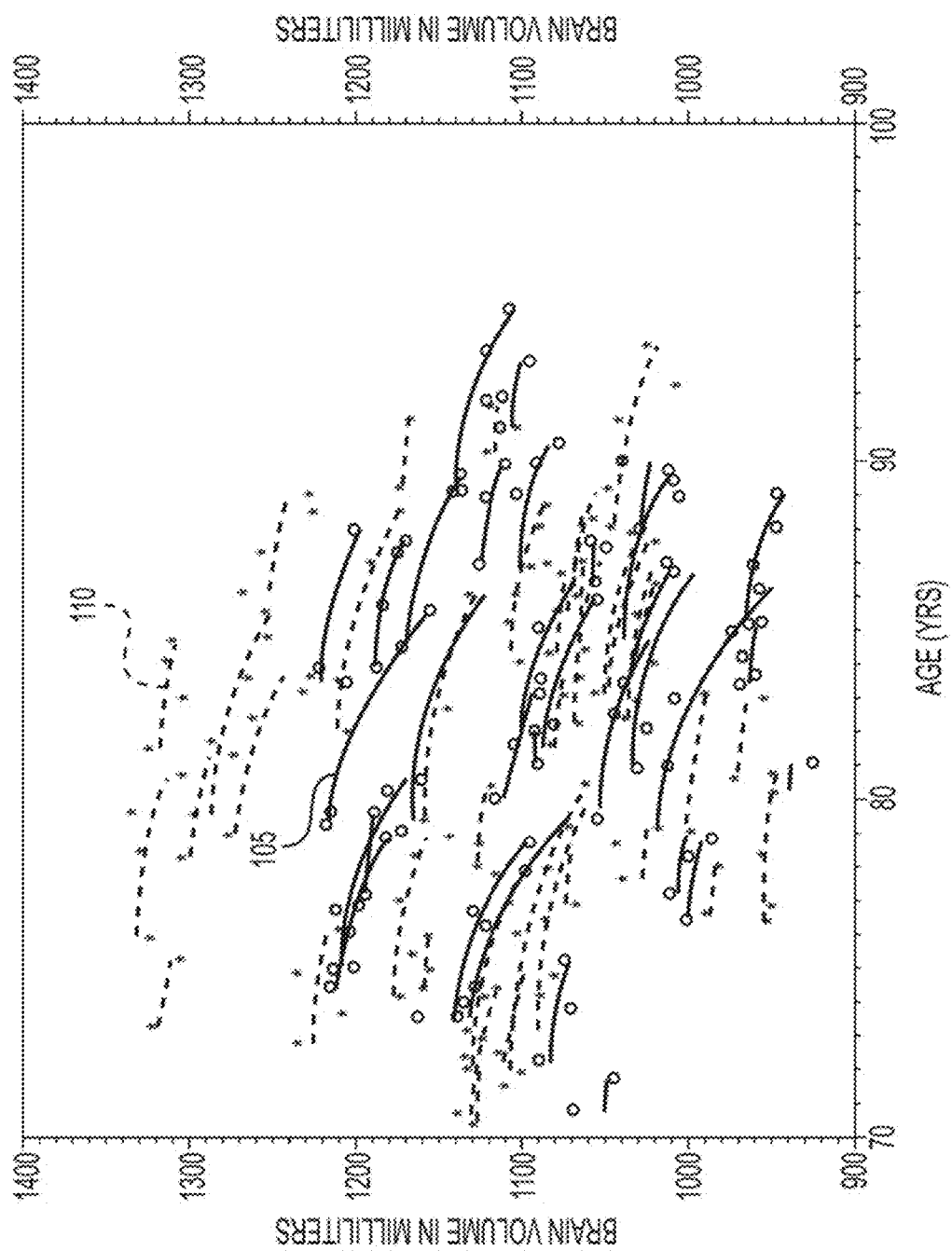
FIG. 1 is an exemplary graph illustrating longitudinal changes in brain volume according to an exemplary embodiment of the present disclosure.

The exemplary system, method and computer-accessible medium, according to an exemplary embodiment of the present disclosure, can be used to calculate the volumetric thickness and density of a cSDH in three-dimensions. An exemplary procedure for the placement of twist drill craniostomy can be guided by volumetric and segmentation analysis and can account for density, thickness and the shape of a cSDH, in order to facilitate better hematoma drainage than the traditional estimation of location.

Thus, the exemplary system, method and computer-accessible medium, according to an exemplary embodiment of the present disclosure, can determine the optimal drainage site for cSDH as a function of distance from the attributes of the subdural hematoma, (e.g. thickest portion, most dependent portion, centroid). Subdural drains placed closer to the centroid of a hematoma can result in optimal drainage. The exemplary system, method and computer-accessible medium, according to an exemplary embodiment of the present disclosure, can also determine the optimal drainage site for cSDH as a function of density throughout the subdural hematoma. Subdural drains placed in regions of the subdural hemorrhage that are less dense on segmentation analysis can result in optimal drainage. Additionally, the exemplary system, method and computer-accessible medium, can determine the optimal placement of a twist drill craniostomy accounting for density, thickness and shape simultaneously. The exemplary analysis of pre and post-operative films from patients who have undergone twist drill craniostomy can reveal that drains placed closer to an optimal location, accounting for density, thickness and shape of a cSDH, have resulted in better drainage than suboptimally placed drains.

The exemplary measure of the outcome of using the exemplary system, method and computer-accessible medium, can include the rate of residual hematoma. Additionally, outcome measurements can include, for example, radiographic (e.g., the amount of progressive cerebral atrophy after drainage, cSDH recurrence), and clinical (e.g., Functional Independence Measure, modified Rankin Scale score, mortality). This can facilitate a procedure that can potentially significantly reduce morbidity and mortality for cSDH in both veteran and civilian populations by improving the efficacy of bedside treatment. The exemplary procedure can be programmed into image viewing software such that the surgeon can see where the optimal drain site is while viewing the images of the cSDH.

Chronic subdural hematoma is an important health problem. cSDH is a condition that primarily impacts the elderly and others with brain atrophy. Its incidence ranges between about 13.5 to about 58.1 per 100,000 persons/year. (See, e.g., References 25 and 46). In the increasingly aging civilian population, studies predict that cSDH will surpass primary brain tumors (e.g., up to 14 per 100,000/year) (see, e.g., Reference 47), and metastases (e.g., approximately 28 per 100,000/year) (see, e.g., Reference 48) to become the most common cranial surgical condition once approximately 20 to 25% of the population is greater than 65 years old. (See, e.g., Reference 46). Among patients treated at VA hospitals, who are disproportionately male and older, cSDH has an incidence of about 79.4 per 100,000 per year, with projections of an incidence rate of about 121.4 cSDH cases per 100,000/year in the VA population by the year 2030. (See, e.g., Reference 25). Age, alcoholism and prior history of traumatic brain injury are risk factors for cSDH that disproportionately affect the veteran population and account for the increased risk relative to civilians.

Alcohol use can increase the risk of chronic subdural hematoma. Department of Defense surveys have found members of the military to have higher rates of heavy alcohol use than civilians. (See, e.g., Reference 49). One study found that veterans of age 61-70 were 73% more likely to report heavy drinking than civilians, even after accounting for demographic differences. (See, e.g., Reference 50). Alcoholism has a significant correlation with the incidence of subdural hematoma: about 14.7% of cSDH patients were alcoholic in Sweden (see, e.g., Reference 51), and about 13% were alcoholic in Spain. (See, e.g., Reference 52). Alcohol can increase risk for cSDH by increasing brain atrophy, impeding liver function resulting in coagulopathy (see, e.g., Reference 53), and impairing balance and judgment, leading to multiple falls and brain injuries.

Traumatic brain injury can increase the risk of chronic subdural hematoma. Traumatic brain injury ("TBI") represents a signature injury of modern warfare, and affects as many as one fourth of injured service members. (See, e.g., Reference 55). Brain injury of diverse etiology can result in regional or global brain atrophy and increase risk for cSDH. (See, e.g., References 53, 55, 56, and 57). Subdural hemorrhage is caused by the tearing of bridging veins between the brain and dura and thus atrophy increases risk. (See, e.g., References 53 and 58). Vascularization of the expanded subdural space, and local inflammation, can contribute to cSDH recurrence. (See, e.g., References 59, 60, 61, and 62).

Despite its growing prevalence, the outcome of cSDH remains poor. Patients treated for cSDH are at risk for intracerebral hemorrhage, seizures, exacerbation of comorbidities associated with the interruption of anticoagulant therapy, and other complications associated with hospitalization of the elderly. Up to 20% of patients have poor neurologic outcomes resulting in significant disability. (See, e.g., References 45, 57, 63, and 64). Perioperative mortality for cSDH ranges from about 1.2% to about 11%. One-year mortality among elderly patients treated with a drainage intervention is about 30% to about 32%. (See, e.g., Reference 26). The mean survival of post-cSDH patients is about 4.4 to about 4.7 years, which is significantly shorter (e.g., hazard ratio of about 1.94, p<0.0002) than the mean of 6.0 years survival computed from actuarial life-tables. (See, e.g., Reference 26). The mortality rate for relatively younger cSDH patients, age 55-64 years, is 17 times the age-matched population rate. (See, e.g., References 45, 57, 63, and 64). The median length of stay for a cSDH is 8 days, which is higher than the median length of stay for age matched patients undergoing brain tumor resection performed by the same neurological service. (See, e.g., Reference 57).

Current treatment for subdural hematoma needs improvement. Generally, chronic subdural hematoma is managed by craniotomy, burr hole or twist drill craniostomy. While chronic subdural hematoma can resolve spontaneously (see, e.g., References 65 and 66), an untreated hematoma can be fatal if it results in mass effect and herniation, or causes a deficit that spirals into medical complications. (See, e.g., Reference 53) Surgical intervention has been shown to improve outcomes and decrease mortality of cSDH, with one estimate adding 3.2 years (e.g., p=0.001) to average survival. (See, e.g., Reference 37). Patients with large cSDHs who undergo drainage have a more complete neurological recovery and less recurrence (e.g., about 15%) as compared to those who do not undergo drainage (e.g., about 26%). (See, e.g., Reference 67). Thus surgery can either be necessary, or have utility, for cSDH management. Three surgical procedures for evacuation of subdural hematomas are in use today: (i) craniotomy, which some surgeons reserve for patients with membranes or loculation confounding cSDH evacuation, (ii) burr hole craniostomy and (iii) percutaneous twist-drill craniostomy ("TDC").

Twist drill craniostomy can be as effective as burr hole craniostomy. However, twist drill craniostomy needs better efficacy. Twist drill craniostomy is often performed at the patient bedside, while burr hole craniostomy and craniotomy are generally performed in the operating room. A meta-analysis of 830 publications prior to 2010 defining the utility of each procedure as a function of recurrence, death, and other complications found burr hole craniostomy to have the best outcomes of the three treatment options by a narrow margin. After correction for selection bias, craniotomies resulted in the most deaths, burr holes resulted in the most nonfatal complications and twist drills had the most recurrence with the least proportion cured. (See, e.g., Reference 41). Increased recurrence of hematomas with twist drills has been previously confirmed (see, e.g., References 42, 43, 44 and 45) and can be partially attributed to suboptimal drain placement. Multiple cohort studies and meta-analyses of studies published after 2010 failed to find a difference in recurrence rates as well as mortality, morbidity, and cure rates (see, e.g., References 29, 30, 31, and 68) between burr hole and twist drill craniostomy. This discrepancy between studies can be explained by the advancement of twist drill craniostomy technology over time, the introduction of new techniques such as irrigation through the catheter and/or increased operator experience as more practitioners adopted this treatment. However, perception among surgeons that twist drills have a high recurrence rate impacts treatment selection. Burr hole craniostomy remains the most broadly popular surgical option for primary chronic subdural hematomas in most reporting countries. (See, e.g., References 43, 69, 70, and 71). 85% of Canadian neurosurgeon respondents to a treatment survey in 2005 preferred single or double burr holes to any other surgical treatment for cSDH. (See, e.g., Reference 43).

Patients undergoing bedside procedures, such as twist drill, can be treated sooner after diagnosis because treatment does not require an operating room time slot and mobilization of a team. (See, e.g., Reference 31). Because twist drill craniostomy requires less anesthetic burden, and is often performed under local anesthesia (see, e.g., Reference 44) it is ideal for treatment of cSDH in the elderly, who are the most at risk for perianesthetic morbidity and mortality. (See, e.g., Reference 72). Twist drill craniostomy can also be economically advantageous since it reduces operating room and equipment cost as well as postoperative care time. A retrospective study found a cost savings of $1770 per procedure (e.g., p=0.05) and a 4 day reduction in length of stay favoring twist drill over burr hole craniostomy in a VA institution. (See, e.g., Reference 31). The reduced length of stay was due to both a shorter interval between diagnosis and treatment, and a shorter postoperative intensive care unit stay. If twist drill technique can be optimized to decreased recurrence rates so that it is unequivocally superior to burr holes, then patients can benefit from faster treatment, decreased anesthesia and shorter length of hospital stay.

The clinical outcome of cSDH drainage can be related to the amount of blood left on the brain. However, the presence of loculations in chronic subdural hematoma does not fully explain cSDH recurrence. Modern treatment for cSDH continues to have high recurrence rates, with an average of about 11% of patients recurring within three years. (See, e.g., References 27, 28, 73, and 74). cSDH recurrence has been attributed to loculations dividing the subdural hematoma into compartments that cannot be accessed with a single drain. (See, e.g., Reference 60). This problem may be addressed with membranectomy of the loculations during burr hole craniostomy or craniotomy in the operating room (see, e.g., References 75 and 76); unfortunately, not all loculations are able to be treated in this manner, and resection of membranes does not have a significant effect on overall cSDH recurrence burden in meta-analyses. (See, e.g., References 29, 30, and 60).

Recurrence can be partially due to the toxic effect of blood break down products on the brain and subdural space. Loculations are likely an indirect factor in recurrence, which can be more directly linked to the amount of remaining hematoma fluid after drainage. This fluid can contain increased concentrations of cytokines, inflammatory mediators and fibrinolytic factors. (See, e.g., References 59, 60, 61, and 62). In addition, factors that can increase the pressure of the hematoma space relative to the underlying subarachnoid layer, such as the presence of subdural fluid and/or air, cerebral atrophy, and cerebrospinal fluid ("CSF") reduction, can delay collapse of the space between brain and dura and prevent brain re-expansion, resulting in increased cSDH recurrence. (See, e.g., References 38, 39, 53, and 77). Thus, the removal of a large amount of subdural hematoma fluid, without introducing air or otherwise enabling maintenance or expansion of the subdural space, can significantly reduce recurrence. A study of 63 cSDH patients treated with burr hole craniostomy demonstrated a significant difference in recurrence rate based on the drainage catheter position, determined by post-hoc imaging analysis. (See, e.g., Reference 39).

Reduced post-operative hematoma volume can be associated with better outcomes. A retrospective study of 140 cSDH patients treated with burr hole craniostomy analyzed the characteristics of the pre- and post-operative CT scans and tracked residual volume, recurrence, and cognitive outcome by the modified Rankin Scale ("mRS"). Residual hematoma thickness was a significant predictor both of good and poor clinical outcomes (e.g., defined by mRS threshold of >2) and of recurrence. This result remained significant on multivariate analysis with several other factors. The difference of mean thickness for good versus poor clinical outcome was about 2.5 mm, and recurrence versus no recurrence was about 2.3 mm. The thickness threshold for poor recovery was about 14 mm. The study did not include quantitative volumetric measures. (See, e.g., Reference 40).

Despite current exemplary procedures, the localization of bedside drainage placement can be improved. Burr hole craniostomy localization can tolerate error better than twist drill craniostomy localization. Burr hole craniostomy can result in a larger diameter opening than twist drill, and thus can facilitate more rapid fluid egress, as well as creating a margin for error. The extra diameter of a burr hole can also facilitate maneuvering of a drainage catheter a smaller amount, in order to optimize drainage location after estimation with the initial burr hole. Twist drill craniostomies are generally arbitrarily and approximately positioned over the cSDH's greatest depth, or sometimes a point near there where gravity can favor drainage. (See, e.g., Reference 78). The decreased diameter of a twist drill hole may not enable drain manipulation to correct for initial inaccuracies in drain placement. Decreased recurrence of cSDH with burr hole versus twist drills can be accounted for by increased capability for maneuvering of the drainage catheter into an optimal position even after suboptimal localization.

Visual estimation of best placement for twist drill craniostomy using a head CT can be difficult. Higher success rates, and lower recurrence rates, with twist drill craniostomy are noted when treating homogenously hypodense rather than mixed density subdural hematomas. (See, e.g., References 78 and 79). Mixed density subdural hematomas are prevalent due to acute-on-chronic rebleeding events, which can deposit blood in several stages of hematoma development over time. (See, e.g., Reference 53). Moreover, unlike epidural hematomas, subdural hematomas, and especially chronic subdural hematomas with mixed density products, do not have a classic "lens" shape that can facilitate the easy distinction of the point of maximal displacement, determined in studies by rigorous calculation (see, e.g., Reference 78) but performed in practice by visual estimation. Thus, the development of a standardized exemplary procedure for determining the point of maximal displacement for complex, challenging subdural hemorrhages can be beneficial. This exemplary procedure can then be used to alter localization of a drain to reduce residual hematoma and recurrences.

Exemplary Methods

Exemplary Patient Selection: The Veterans Affairs, New York Harbor Healthcare (e.g., VISN03) database was searched for digital CT head or brain exams performed from 2004 to 2014. All patients with at least 4 CT scans extending over a period of 1 year or more were selected. Medical records of selected patients were then searched and reviewed to identify 33 patients diagnosed with probable AD. The remaining patients deemed to be free of dementia were on the average younger than the AD group. The lower limit of age for control subjects was then increased in intervals of 3 years till both AD and non-demented patients matched on baseline age. A total of 72 patients, 33 under AD category and 39 under non-AD category were identified, with 191 exams for AD patients and 245 exams for the non-AD group. The whole brain, cerebral spinal fluid ("CSF"), intracranial space volumes and brain radiodensity were measured on 4-12 CT exams. Longitudinal measures were then related to disease status and time since first scan using hierarchical models. In order to demonstrate optimal drainage location in subdural hematoma, 4 patients with varying amount of subdural hematoma were selected.

Exemplary CT Protocol: All CT scans were obtained on Toshiba Aquilion 16 or Aquilion 64 helical scanners (e.g., Toshiba, Tustin, Calif.). Acquisition parameters were as follows: (i) peak tube voltage 120 kVp, (ii) x-ray tube current 150-300 mAs, (iii) field of view 20-25 cm yielding in-plane resolution about 0.790-0.463 mm, (iv) soft-tissue reconstruction kernel FC64 (e.g., 377 exams for 61 patients, 27 with AD) or FC67 (e.g., 59 exams for 11 patients, 6 with AD), (v) matrix size 512×512, (vi) 28-35 slices (e.g., 10th and 90th percentile) (e.g., Range: 24 to 368; 16 studies with >100 slices [161 to 368 slices] and four studies with 24 to 26 slices), and (vii) axial-slice thickness 4.6-5 mm (e.g., 10th and 90th percentile) (e.g., Range: 0.45 to 5.00 mm).

Exemplary Preprocessing of CT scans: In order to eliminate variability that can result from the use of different CT reconstruction methods (e.g., kernels), for each subject, images computed with the kernel that was employed in the highest number of exams for this subject were selected.

Exemplary Image Analysis Procedure: Total intracranial and total brain volumes were assessed using locally developed fully automated software, with no operator intervention. In the first procedure, intracranial space ("ICS") was segmented. For ICS the exemplary procedure can select voxels with CT attenuation in the range of about [−500,+125] Hounsfield units ("Hu"), perform morphologic erosion (e.g., a two-dimensional or three-dimensional erosion) of about 6 mm radius that can disconnect the extra cranial soft tissue from the interior of the cranial cavity, can retain the largest connected component and end with constrained morphologic dilation. The CSF volume was then separated from the brain tissue by selecting all ICS voxels with attenuation values within the fluid range, (e.g., below 16 Hu). The threshold of about 16 Hu was selected by a multimodality CT/MRI optimization study using $T^2$-weighted images as the gold standard for CSF volume. (See, e.g., Reference 10). CSF masks included the entire ventricular and sulcal space. CT attenuation values of all brain voxels were then averaged as brain radiodensity and for all CSF voxels as CSF radiodensity. No coregistration procedures or other normalization procedures were used. All volumes reflected absolute measurements in milliliters, and attenuation values were expressed in Hu. For the subdural hematoma patients, the lesion on CT scans was manually segmented.

The exemplary segmentation analysis according to an exemplary embodiment of the present disclosure can be performed on pre-drainage CT scans, which can include, e.g. (i) the segmentation of subdural hematoma from rest of the soft tissue, (ii) the calculation of the slice of maximum subdural hematoma, (iii) the determination of centroid on the slice with maximum hematoma volume, and (iv) the determination of the point on skull nearest to centroid (e.g., test location). This scan can then be co-registered with a post-drainage CT scan (e.g., by using rigid, also known as Euclidean transformation). The actual location of the twist drill craniostomy can then be determined relative to the post-drainage CT scan and the distance between actual twist drill location and test location was calculated. The post-drainage CT scan can be processed separately to calculate residual subdural hematoma volume.

Figure 7:
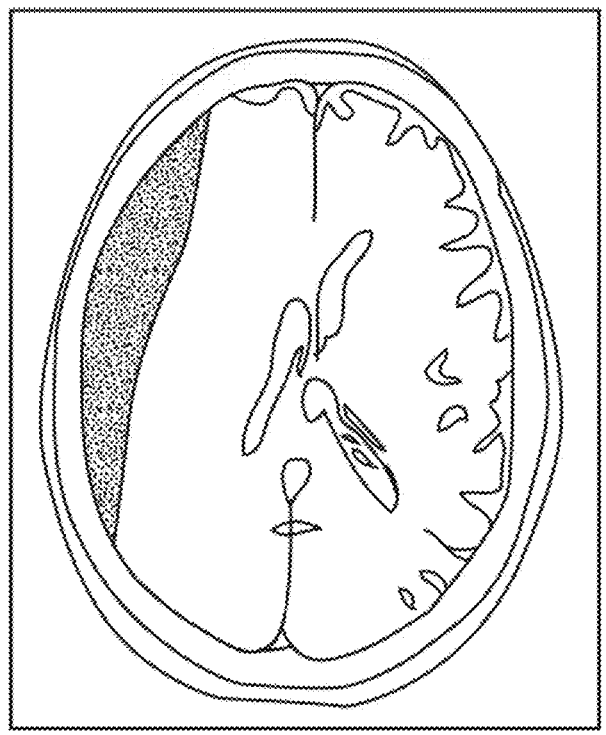
FIG. 7 is an exemplary image of exemplary results of an SDH segmentation on CT images according to an exemplary embodiment of the present disclosure.
Figure 8:
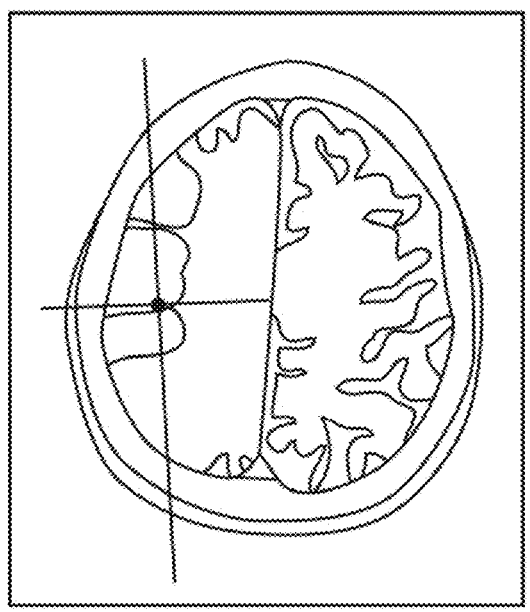
FIG. 8 is an exemplary image of the exemplary calculation of the centroid and a major and minor axis of a subdural hematoma according to an exemplary embodiment of the present disclosure.

The exemplary SDH segmentation can be performed manually. For example, FIG. 7 shows an exemplary image of the typical results of the exemplary segmentation procedure. FIG. 8 shows an exemplary image of the centroid calculated, the mathematically determined point to be drilled, and the major and minor axes. An exemplary relationship between distance of drainage sites from mathematically determined reference sites and residual hematoma volume is suggested.

The population of the VISN03 regional VA system with a recorded head CT without prior hemorrhage was filtered for patients who had a record of twist drill craniostomy procedure performed any time after their first head CT. Four patients who underwent twist drill for cSDH were identified. With the exception of one patient, all procedures were performed at the bedside. Patients were excluded if they did not have any head CT scans at most 3 days before and 3 days after their drainage procedure. The DICOM files for the head CT scans of all four patients were available, de-identified and downloaded.

For example, 4 patients were selected at random from the group described above. Using the exemplary procedures described above, pre and post drainage CT images were processed, and total cSDH volume, slice with maximum blood volume, the centroid of the slice with maximum volume and the point on skull closest to centroid (e.g., test location) were determined. The distance from test location to the point of insertion of the twist drill craniostomy was obtained. The volume of the subdural hematoma before and after drainage was calculated.

The displacement of the actual hematoma drainage site, extrapolated from the post-drainage CT on to the equivalent position of the skull on the pre-drainage CT, was determined as a coordinate of the X, Y, and Z axis of the head CT, using the centroid as the frame of reference (0,0,0). The most posterior (e.g., along the Y axis) point of the subdural reaching the skull's surface was also determined by its coordinate value. The displacement along the Y axis, and the three-dimensional distance between this posterior point and the actual twist drill placement site, was measured in millimeters. Correlation of the pre-drainage volume, the post-drainage volume, the amount of hematoma drained, the X, Y, and Z displacement between the actual and posterior site and the distance between the actual and posterior site was determined by linear regression. In this limited analysis of four patients, the amount of hematoma drained did not achieve significant correlation with distance from the centroid; however power analysis of the data suggested increased numbers (e.g., as few as n=35) might enable that achievement.

Exemplary Brain Atrophy

Brain atrophy rate can be an objective outcome measure. CSDH patients have greater atrophy than normally aging controls but lower atrophy than Alzheimer disease patients. In order to assess cerebral atrophy over time, an exemplary data mining procedure was used, by selecting from image archives of a VA hospital system all CT exams relevant to the exemplary hypothesis. The regional VISN03 database was searched for digital CT head or brain exams performed from 2004 to 2014. Of all patients with an index CT scan of the head during this period, patients were excluded if: (i) they had fewer than three subsequent CT scans, (ii) serial scans extended over less than 1 year or (iii) they were diagnosed with hydrocephalus or any other neurodegenerative disease. Patients were deemed to have Alzheimer's disease if they meet NINCDS-ADRDA criteria for probable AD (see, e.g., Reference 80) as determined by the treating physician. Review of medical records identified 48 such patients. Patients having a cSDH were defined if they had a diagnosis of ICD9 code 432.1 or 852.2 entered by a physician documenting the purpose of the patient's consultation within the hospital system. 50 such patients were identified. Of the remaining patients with similar longitudinal imaging history, but free of any neurodegenerative diseases, and hydrocephalus, review of medical records yielded 70 age matched controls. Thus, a total of 168 patients, 48 in the AD category, 50 in the cSDH group and 70 in the control category were selected, with 1416 CT head scans in total.

Exemplary Automated Analysis of Brain Atrophy

Total intracranial and total brain volumes were assessed using locally developed fully automated software, with no operator intervention. In the exemplary procedure, ICS was segmented. For ICS, the exemplary system, method and computer-accessible medium, can select voxels with CT attenuation in the range [−500, +125] Hounsfield units (Hu). This can exclude bone and air. Then, on the remaining soft tissue, 3D morphologic erosion of about 6 mm radius can be performed using the exemplary system, method and computer-accessible medium, that can disconnect the extra-cranial soft tissue from the interior of the cranial cavity. After, the largest connected component can be retained that results in the exclusion of extra-cranial soft tissue. Additionally, constrained morphologic dilation can be performed on the retained component resulting in the recovery of all intracranial space voxels. The CSF volume can then be separated from the brain tissue by labelling all ICS voxels with attenuation values within the fluid range, (e.g., below 16 Hu as CSF). The ICS voxels not classified as CSF can be labeled as brain tissue. The threshold of 16 Hu was selected by a multimodality CT/MRI optimization study using T2-weighted images as the standard for estimating CSF volume. (See, e.g., Reference 37). CSF masks included the entire ventricular and sulcal space. No coregistration techniques or other normalization techniques were used. All volumes reflected absolute measurements in milliliters. All attenuation values were expressed in Hu. All statistical analyses were carried out using Statistical Package for the Social Sciences (SPSS version 21, IBM Corporation, Armonk, N.Y., USA).

Figure 9:
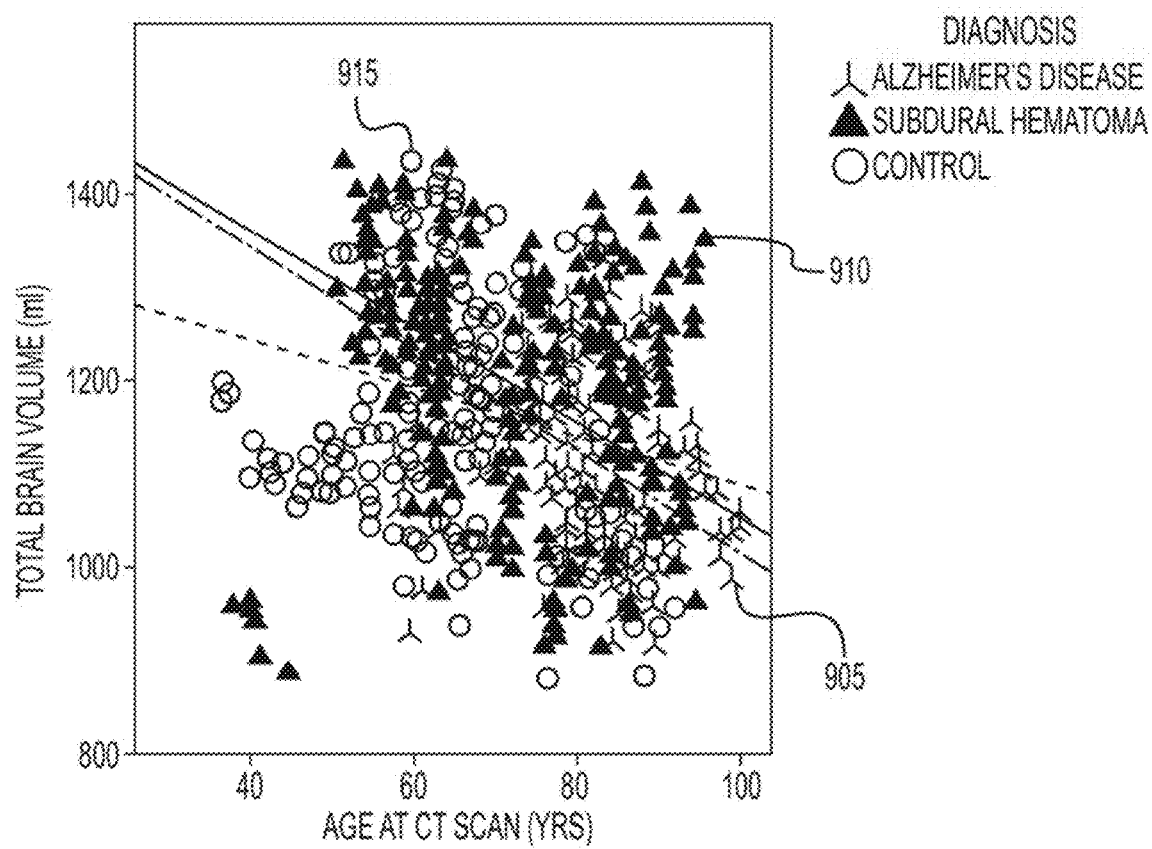
FIG. 9 is an exemplary graph illustrating the changes in the brain volume over time according to an exemplary embodiment of the present disclosure.

A total of 1416 CT scans for 168 patients (50 SDH, 48 AD and 70 controls; ages 19 to 95 years) with an average of 8.4 exams over 5.2 years were analyzed. The atrophy rate dA/dt differed significantly across three groups. (See, e.g., FIG. 9; showing Alzheimer's disease 905, subdural hematoma 910 and control group 915). The overall p-value<0.001. The average dA/dt in AD was 7.59 ml/year, 3-fold higher than in controls (2.34 ml/year; intergroup p-value<0.001). In cSDH patients the mean dA/dt was 4.93 ml/year, about twice that of controls (p-value=0.015).

Exemplary software can be used that not only detects the size and shape of a chronic subdural hematoma, but where the twist drill entry point is in relation to the subdural hematoma. The exemplary system, method and computer-accessible medium, according to an exemplary embodiment of the present disclosure, can determine the drainage point in the skull that can result in the least residual hematoma volume after drainage as a function of distance from the hematoma centroid and accounting for gravity.

Patient Population

A preliminary search through the VA Informatics and Computing Infrastructure ("VINCI") of the entire VA system was performed using CPT codes 61105 and 61108, which are used in the VA for twist drill craniostomy evacuation of subdural hematomas. 583 patients across the system were identified. It is estimated that at least 270 of these patients will have sufficiently complete pre and postoperative records, including imaging, for inclusion in the exemplary study. Inclusion criteria can include, e.g., (i) a head CT less than 1 day prior to the twist drill procedure, (ii) less than 3 days after the twist drill procedure, and (iii) record of physical therapy assessment including Functional Independence Measure and sufficient records to calculate a modified Rankin Scale score. Patients with bilateral hematomas were included, and if both hematomas were drained in a procedure, the larger side was be included in the study, and the other side may only be noted as a secondary descriptive measure, and not included in the main analysis. Exclusion criteria include: (i) refractory coagulopathy, and (ii) known cause of intracranial hypotension resulting in refractory cSDH. Preference for inclusion was granted to patients with longer versus shorter follow-up. Since one-third of patients with treated cSDH will have died within one year treatment, death will not be an exclusion factor for this study.

Characteristics of the initial cSDH: cause of subdural hematoma, date of diagnosis, date of evacuation, laterality/ bilaterality, measured maximum subdural hematoma thickness, average intensity on CT (e.g., hypodense, isodense, hyperdense)

Figure 10:
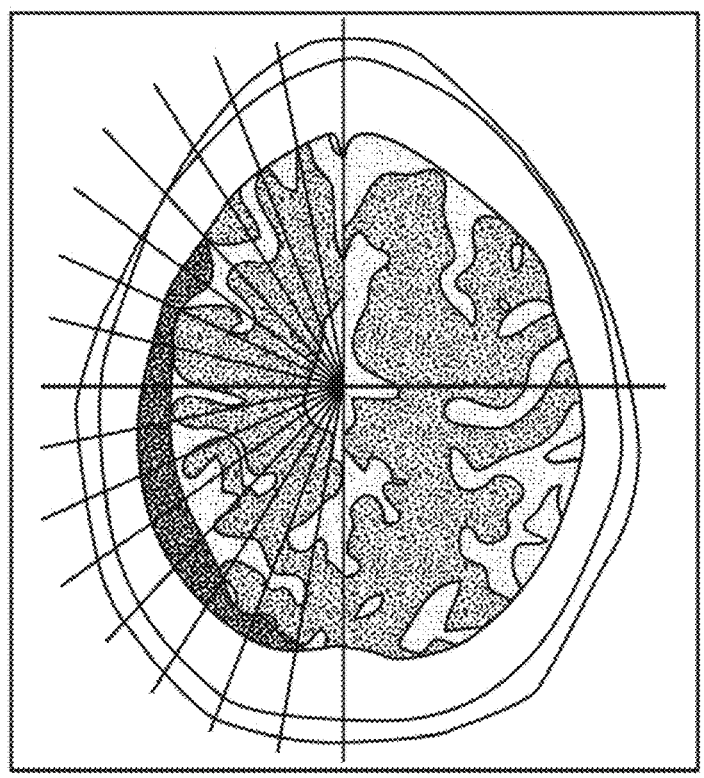
FIG. 10 is an exemplary image of an exemplary segmentation procedure according to an exemplary embodiment of the present disclosure.

Exemplary Treatment: twist drill craniostomy insertion details regarding whether dura was opened with drill or with a separate instrument, whether cSDH egressed spontaneously under pressure or only after drain placed to bulb suction, head of position (e.g. flat, 30 degrees or unrestricted) after placement, activity restriction (e.g., bed rest versus up ad lib after placement) An imaging analysis program was to analyze each DICOM image. Image segmentation analysis was employed to isolate the subdural hematoma shape. (See, e.g., FIG. 10).

cSDHs can have a complex mixture of hyperdense, isodense and hypodensity, with most having some component of mixed density. Some of these mixed density subdural hematomas can be distributed by gravity, some can be sporadically distributed throughout the hematoma and some can form layer patterns along the edges of the subdural hematoma. Many of the hematomas can be bilateral. Some can be anteriorly located, making the shape of the subdural more complex than a convex crescent. All of the images after drainage can have CT artifacts at the level of the metal drain. Difficult images can be manually identified, and the researchers will collaboratively work with the programmers to improve and quality test the procedure to accommodate these complexities. The diversity and challenges in this image set can facilitate a robust processing program to be created that can reliably interpret radiographically difficult head CTs for eventual practical use.

Exemplary Drain Site Procedure

Figure 11:
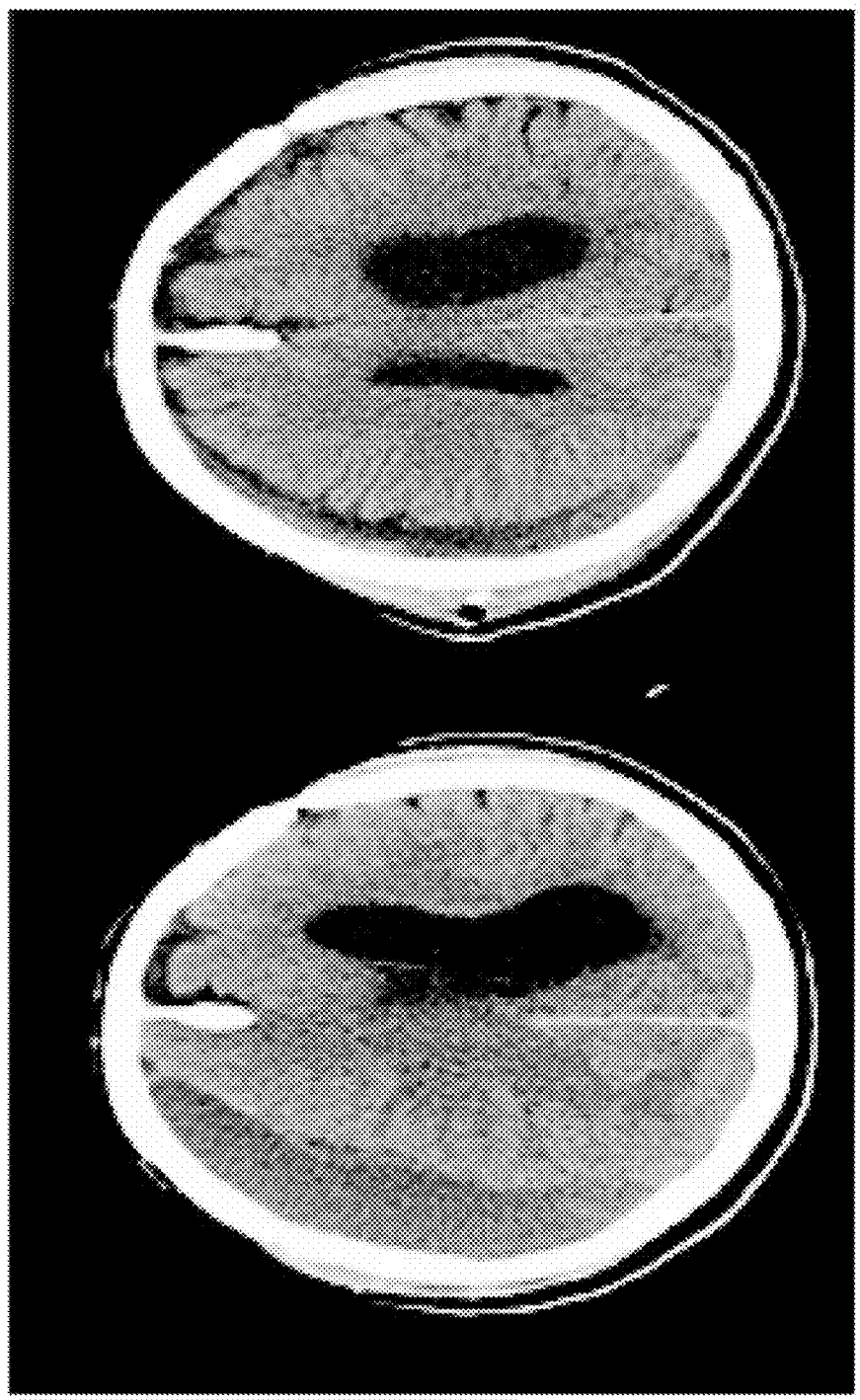
FIG. 11 is a set of exemplary images of exemplary axial CT scans according to an exemplary embodiment of the present disclosure.

The position of the subdural drain can be compared to the mathematically computed point of maximal displacement. (See, e.g., exemplary image shown in FIG. 11). This can be defined as the greatest distance between all compared points of this shape orthogonal to its cerebral side and orthogonal to its cranial side, with minimized minor geometric error.

The point of maximum thickness can underestimate the effect of complex subdural hematoma geometry on its drainage. The centroid of the subdural hematoma can be calculated. The centroid can be defined as the average X, Y, Z coordinate value for all points (e.g., voxels) that can lie within the borders of a subdural hematoma. This can be a geometric reference point for the "center of mass" that can be difficult to estimate visually. As further descriptors of the shape, the major and minor axes of the subdural hematoma can be identified. These axes can be defined mathematically given the segmentation mask. (See, e.g., Reference 81). The vector originating at the centroid and directed along the minor axis can intersect with the skull at another potential drain placement site.

Exemplary Drain Site Procedure

The exemplary system, method and computer-accessible medium, according to an exemplary embodiment of the present disclosure, can affect the size of residual (e.g., post-drainage) cSDH. This can be assessed on the first CT scan performed after removal of the twist drill craniostomy drain using the volumetric segmentation analysis described in the preliminary data. Drains placed closest to the hematoma centroid can have lowest residual hematoma. Other factors influencing this result can include gravity and bed position, which can be noted and accounted for with multivariate regression.

The exemplary system, method and computer-accessible medium, according to an exemplary embodiment of the present disclosure, can affect the rate of progressive cerebral atrophy. Patients with cSDH have a higher rate of progressive cerebral atrophy than normal controls, but a lower rate than dementia patients. The relationship between both adequacy of drain placement and residual hematoma on progressive atrophy can be assessed.

The exemplary system, method and computer-accessible medium, according to an exemplary embodiment of the present disclosure, can illustrate that suboptimally placed drains, which can be co-linear with drains resulting in increased residual hematoma, can result in higher progressive atrophy than optimally placed drains and less residual hematoma. Cognitive capability and physical capacity (e.g., dementia comorbidity and FIM) can be affected, since patients capable of doing less should have higher atrophy rates.

The drainage site can be determined, for example, using the following exemplary procedure. For example, one or more CT images can be taken, and can be used to identify the subdural hematoma. The attributes of the subdural hematoma can be calculated (e.g. a centroid, a density weighted centroid, a major axis, a minor axis, a topmost part of the subdural and/or the most dependent part of the subdural hematoma). The treatment can then be optimized based on these attributes (e.g. the tube to drain subdural hematoma can be placed at a point on skull closest to centroid determined).

The exemplary system, method and computer-accessible medium, according to an exemplary embodiment of the present disclosure, can also be used to treat other lesions on the surface of the brain. This can include, for example, draining other hematomas on the surface of the brain (e.g. epidural hematoma), draining fluids (e.g. subdural hygroma), aspiration of abscess or other viscous material, and/or solid lesions that can be mobilized (e.g., a lesion that can be small enough to start with, can be chopped into smaller pieces, or its consistency can be changed by injecting something making it amenable to aspiration/removal through the drain, needle, or tube).

The location of a subdural hematoma or the lesion in the CT can be automatically determined, for example, using the exemplary system, method and computer-accessible medium. Additionally or alternatively, the location of the subdural hematoma can be determined by a person (e.g., a doctor), and the location can be transmitted to/received by the exemplary system, method and computer-accessible medium.

Exemplary attributes of the hematoma can include, for example, a centroid, density weighted centroid, a major axis and a minor axis of the lesion, topmost or bottommost portion, or areas of interest the description of which follows. The density-weighted centroid can be a centroid that can weight areas of different intensities on a CT scan differently. For example, it can weight areas with more intensities more and can weight areas with less intensities less, or vice versa. The weight of these intensities can be further modified by some factor; for example areas of twice as high intensity as some other area can be weighted four times (e.g., a factor of two) as much as the other. The areas of interest in the subdural hematoma can include the location of septa, or the areas where density changes sharply. The attribute determination can be based on, for example, location, shape, type, or presence or absence of septations in hematoma.

Using the exemplary attributes as determined above, the drainage site can be determined. This determination can be based only one single attribute (e.g. location on the skull that's closest to the centroid), or on the combination of attributes (e.g. location on the skull that is in between the centroid and the most dependent part of the subdural). The location of the drain or needle, or other instrument being used for treatment, can be on the surface of the skull or inside the lesion itself. In case of a drain penetrating the lesion, the orientation can be along the major or minor axis.

The optimum location can be determined by conducting a study that can correlate the actual drainage site to the outcome in that patient. For example, the optimal drainage site can be the site that can minimize the residual amount of the lesion, or a specific portion of the lesion, determined to be most clinically relevant. The optimal drainage site can also be the one that minimizes recurrences, length of stay and/or disability. The correlation can be performed using linear regression, neural networks, or various other statistical or machine learning procedures that will be apparent to those skilled in this area upon reading this.

The exemplary system, method and computer-accessible medium, according to an exemplary embodiment of the present disclosure, can affect recurrent cSDH. Patients can be assessed for recurrence within one and three years. Recurrence can be defined as symptomatic cSDH with the same laterality as the cSDH that was initially treated in the study. Expected results can be that suboptimal drain placement, collinear with increased residual hematoma can increase recurrence risk. Confounders of this measure can be resumption of anticoagulation, extent of atrophy and likelihood of repeat trauma.

The exemplary system, method and computer-accessible medium, according to an exemplary embodiment of the present disclosure, can affect functional independence measure or FIM. Physical therapy in the VA system records this measure on the vast majority of cSDH patients seen in the VA and thus it can provide an objective assessment of capability. FIM can be assessed on the last patient visit by physical therapy prior to discharge from the hospital. Suboptimal drain placement can be expected, which can be collinear with increased residual hematoma, can correlate with reduced FIM score. The major confounder of FIM can be pre-morbid condition since patients with poor capabilities preoperatively at baseline can be unlikely to perform better than baseline after cSDH treatment.

The exemplary system, method and computer-accessible medium, according to an exemplary embodiment of the present disclosure, can affect a Modified Rankin Scale score ("mRS"). While the mRS may not always be recorded in the veteran's medical record at the time of injury it is a simple six-point scale that can be reconstructed based on a review of records with reasonable accuracy. mRS can be assessed at one and three years after cSDH drainage. It can be expected that the suboptimal drain placement can be collinear with increased residual hematoma will correlate with increased mRS score (e.g., a score of 6, the highest possible=dead). Confounders of mRS can include patient comorbidities.

The exemplary system, method and computer-accessible medium, according to an exemplary embodiment of the present disclosure, can affect duration of survival, or interval between cSDH treatment and death. Death can be determined by assessment of the medical record and IRB approved access to a VA benefits database, which is known to be more accurate for reporting of death than the medical record.

Exemplary Determining the Optimal Drainage Site for cSDH as a Function of Density Chronic subdural hematomas can vary in density, partially due to rebleeding, which can result in great variation of hematoma content due to differences in stages of blood coagulation. The viscosity of the subdural hematoma at different sites can be highly variable. This variation can be correlated with image intensity on CT. Whether drain placement closer to less dense and more fluid components of the hematoma can result in better drainage can be determined.

The patient recruitment, data collection, image segmentation analysis, power analysis and statistical analysis can be the same as described above. The exposure can be the average density of the subdural hematoma contents around the drainage site. The results can be similar to those described above.

Exemplary Determining the Effect Size of the Contributing Factors of Shape, Thickness and Density The cohort, period of follow-up, and outcomes can be the same as described above. However a further exemplary goal can be to determine the effect size of these contributing factors using exemplary machine learning procedures. Once the effect size has been evaluated, the exemplary procedure can be optimized in an iterative fashion, accounting for the relative impactors.

Exemplary Procedure for Optimization and Machine Learning

Machine learning or various other statistical and image processing procedures can be used to arrive at an optimized drain placement site based on the multiple factors being considered. The procedure can be tested on a separate cohort of patient samples not used to build the model and, once fully optimized, can be integrated into image viewing software currently used by neurosurgeons to diagnose cSDH and assess for drain placement.

Exemplary Statistical Considerations

Initially, a univariate analysis can be used to estimate and derive about a 95% confidence interval for correlation of the residual hematoma volume associated with the actual site to centroid distance and evaluable competing risk factors such as age and volume of pre-drainage hematoma. Power analysis (e.g., described below) can suggest that a sample size of 270 patients (e.g., each with one pre-drainage and one post-drainage scan) will be sufficient.

The density weighted centroid can be calculated, and the correlation between residual hematoma volume and the actual site to density-weighted centroid distance can be estimated while adjusting for the above mentioned risk factors.

The exemplary system, method and computer-accessible medium, according to an exemplary embodiment of the present disclosure, can utilize the addition of shape of the hematoma to the simple and density weighted centroid measurements described above. Shape can be treated as a four level categorical variable. The first step procedure can to perform one way ANOVA to determine its effect on residual hematoma volume. Then, the best drainage site can be identified as the one minimizing the residual hematoma as a function of drain site, density and thickness as numerical variables and shape as a categorical variable while accounting for above mentioned competing risk factors.

The optimum site can be validated on a separate cohort of 30 subjects in the following exemplary procedures: (i) scans can be processed and the optimum site will be calculated, (ii) residual hematoma for each scan can be predicted for that optimum site, shape, density and volume of the hematoma using linear regression, (iii) residual hematoma and the location of actual site can be determined, and (iv) the residual hematomas resulting from actual drain placement can be compared to predicted residual hematoma that can have had resulted by placing the drain at the optimum location. All statistical tests can be conducted at the 5% significance level using the Statistical Package for the Social Sciences (SPSS version 19, IBM Corporation, Armonk, N.Y., USA) for or MATLAB r2016a (Mathworks Inc., Natick, Mass., USA).

Exemplary Power Analysis and Sample Size

For an exemplary model building, sample size was calculated for linear regression to provide a power of about 80% while having a chance of type 1 error of about 5%. S minimum correlation of about 15% between residual hematoma volume and linear predictors can be detected. Analysis suggested that a sample size of about 270 patients can be adequate for a two-tailed analysis with significance of about p<0.05. For shape as a four level categorical variable, the sample size of about 270 patients can be sufficient to provide an about 80% power to detect an effect size of about 0.20 with an about 5% chance of type 1 error. The exemplary resulting model can be validated in a separate cohort of 30 subjects not previously studied and compare the decrease in residual hematoma resulting from actual drain site to projected decrease in hematoma volume that could have resulted from placing a drain at an optimum site.

Exemplary Drain Site Procedure: The Hounsfield unit density of the subdural hematoma in each axial head slice can be plotted on a three-dimensional coordinate array. From the coordinate of the drain placement site, the total Hounsfield unit density of a spherical area around the insertion site can be calculated at a varying radius in the pre-drainage head CT.

Exemplary Compensation For Instrument Miscalibration: To reduce the temporal variability (e.g., the exemplary scanners were not calibrated daily against a phantom) the component of the brain volume ("BV"), CSF, cerebral spinal fluid volume ("CSF-V") and brain radiodensity ("BR") that could be explained by the lack of calibration was removed. This was performed by linearly regressing BV, CSF-V and BR against average ICS radiodensity. This yielded adjusted whole brain volume ("Bv'"), adjusted CSF volume ("CSF-V'") and adjusted brain radiodensity ("BR'"). The adjusted ICS volume ("ICS-V'") was defined as the sum of adjusted CSF-V' and BV'. The normalized brain volume ("nBV'") was defined as BV'/ICS-V'.

Figure 2:
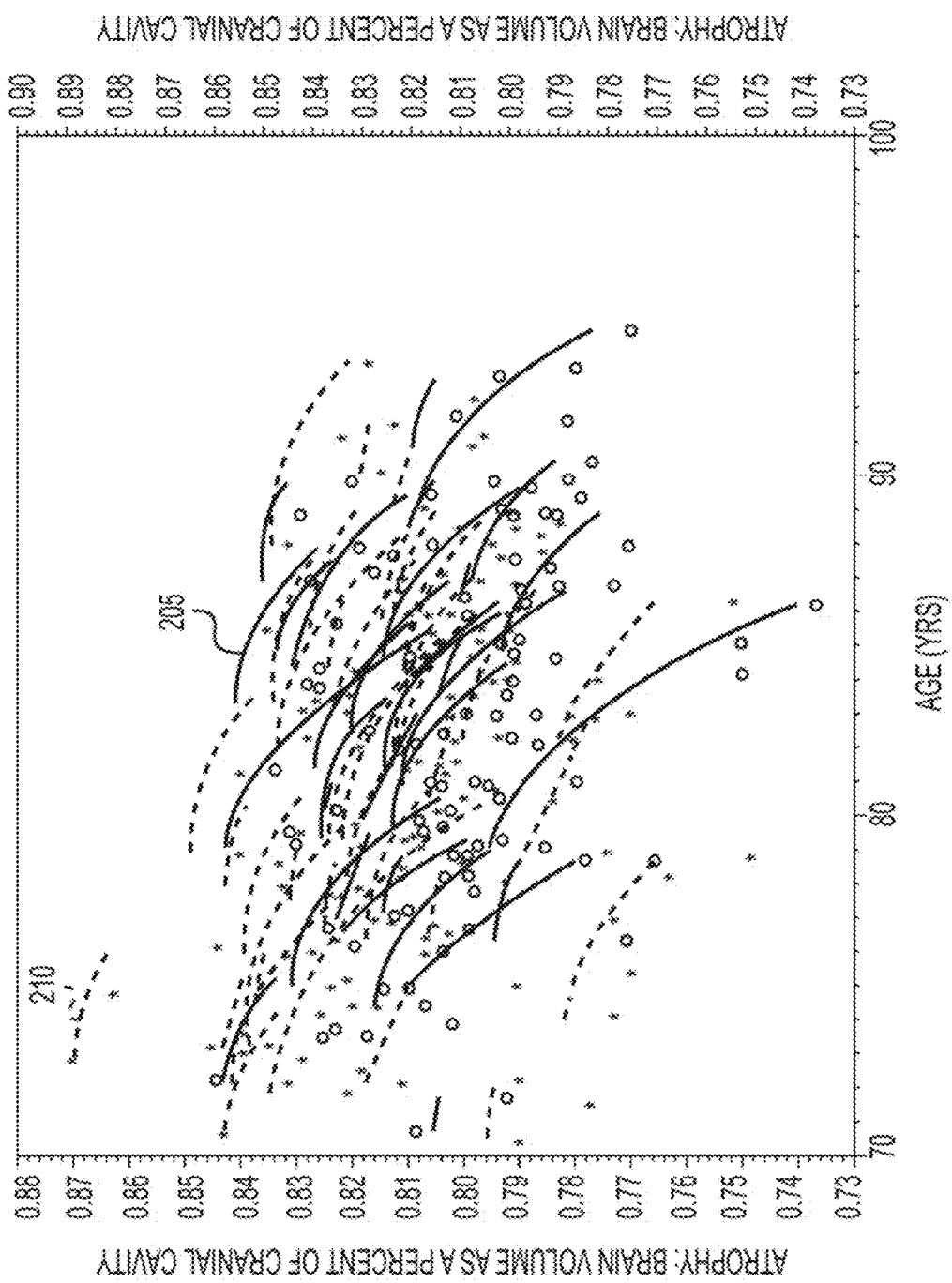
FIG. 2 is an exemplary graph illustrating the data from FIG. 1 with brain volume expressed as a percent of cranial activity according to an exemplary embodiment of the present disclosure.
Figure 3:
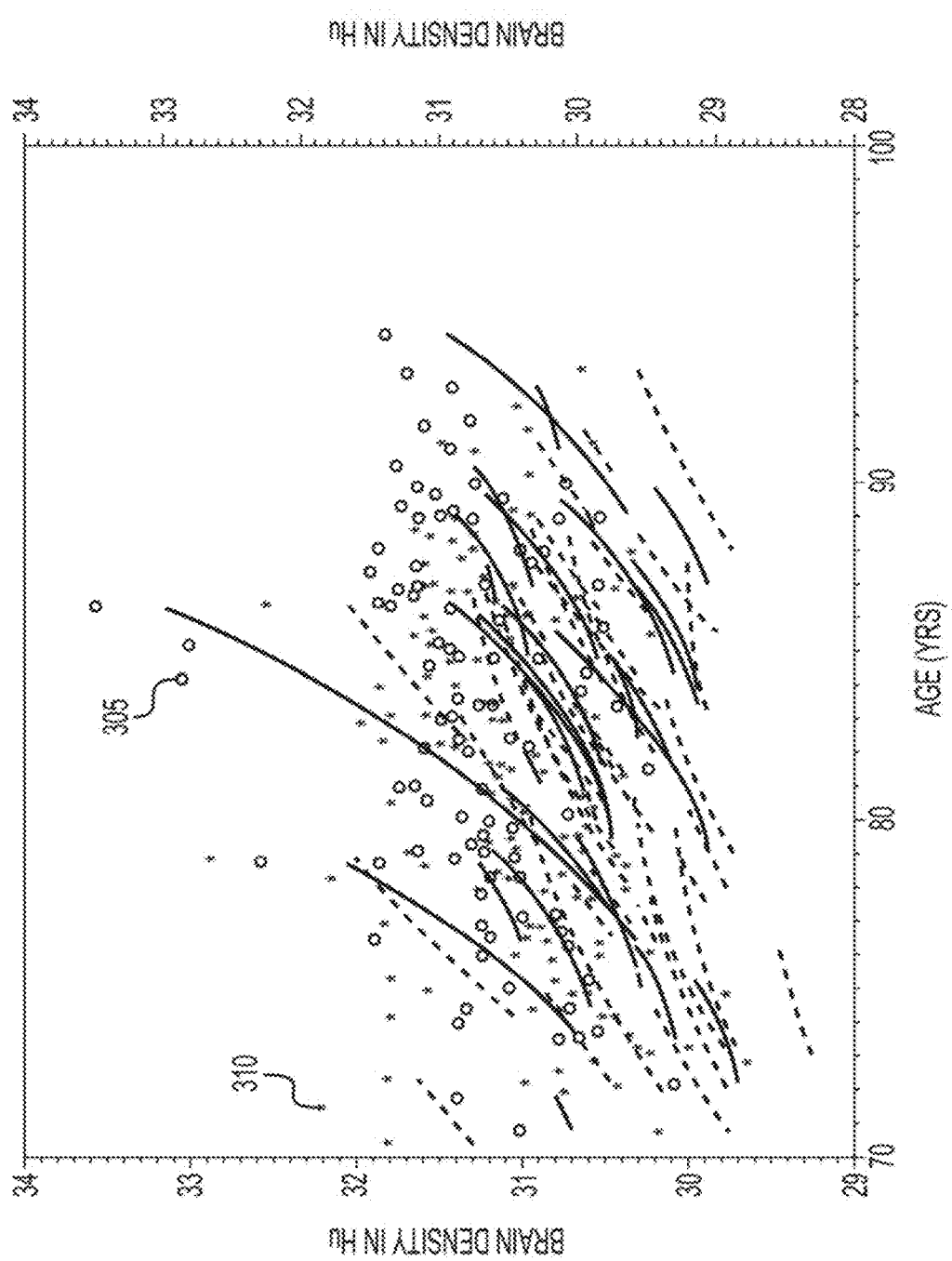
FIG. 3 is an exemplary graph illustrating changes in brain radiodensity according to an exemplary embodiment of the present disclosure.

Exemplary Statistical Analysis: All statistical analyses were carried out using Statistical Package for the Social Sciences (e.g., SPSS version 21, IBM Corporation, Armonk, N.Y.). FIGS. 1-3 were constructed using SAS version 9.4 (e.g., SAS Institute, Carry, N.C.).

Exemplary Test Retest Reliability Of CT Scan: In order to estimate test retest reliability of volumetry on CT scans, the information, that for each patient intracranial cavity size remains constant over time, was utilized. Thus, two-way Intraclass correlation coefficient was calculated for absolute agreement. To avoid missing values, Intraclass correlation coefficient was computed for the first four CT exams only.

Exemplary Estimation Of Brain Parenchyma Atrophy Rate: To analyze time series data with unequal follow up duration and correlated error terms, separate multilevel mixed (e.g., hierarchical) models were developed for BV', nBV' and BR' using a SPSS Mixed procedure. For BV', and nBV', the models related the target measurements to group membership and its interaction with follow-up time (e.g., quadratic term only) as fixed effects. Intercept and slope (e.g., the linear term, time since first scan) were allowed to vary between individuals. Since both groups had comorbidities such as cerebrovascular accidents, head trauma or cerebral edema that might affect the linear term, only the quadratic term may be a fixed effect. Both models were constructed using restricted maximum likelihood estimation.

Exemplary Estimation Of Change In Brain Radiodensity Over Time: For BR', the exemplary system, method and computer-accessible medium, according to an exemplary embodiment of the present disclosure, related the brain radiodensity to Alzheimer disease status and the interaction of Alzheimer disease status with time since first scan (e.g., both linear and quadratic terms) as fixed effects. The intercept and the linear term were allowed to vary between individuals. Covariance structure was first order autoregressive for group level (e.g., fixed) effects, and unstructured for individual level (e.g., random) effects. An exemplary model was constructed using restricted maximum likelihood estimation.

Brain volume loss accelerated over time in both AD and non-AD patients. Rates of acceleration in volume loss were estimated to be 0.86 ml/yr$^2$ [0.0578%/yr$^2$] (e.g. 95% confidence interval ("CI") 0.64 to 1.08 ml/yr$^2$; [0.0389%/yr$^2$ to 0.0767%/yr$^2$]) for Non-AD patients and were 1.32 ml/yr$^2$ [0.0919%/yr$^2$] (e.g. 95% CI 1.09 to 1.56 ml/yr$^2$; [0.0716%/yr$^2$ to 0.1122%/yr$^2$]) for AD patients. Both groups differed significantly in their acceleration (e.g., intergroup p-values=0.006 and 0.017). The brain radiodensity increased linearly by 0.15 Hu/year (e.g. 95% CI 0.065 Hu/year to 0.230 Hu/year; p-value=0.001) for Non-AD patients while it accelerated by 0.017 Hu/yr$^2$ (e.g. 95% CI 0.000181 to 0.033793; p-value 0.048) for AD patients of similar ages. CT volumetry showed an excellent (e.g., ICC=0.996) test-retest reliability.

Brain volumetry on CT is at least as precise as MRI. Longitudinal measures of accelerated volume loss can be used to monitor the progression of AD. Brain radiodensity measured on CT scan can be another potential biomarker for AD, and can reveal insights into the disease mechanisms.

The brain atrophy rate can be used to predict the course of Alzheimer's disease, vascular dementia, normal pressure hydrocephalus, post traumatic dementia, post infectious atrophy, Creutzfeld-Jacob and other neurodegenerative diseases.

Exemplary Results

AD stage can be inferred from the distribution of MMSE scores at the last exam. (See, e.g., Table 1 below). Four AD patients were blind and two were aphasic, which resulted in relatively low MMSEs. The indications for CT scans are given in Tables 2-4 below. The descriptive statistics are given in Table 5 below. All patients were males. Between 4 and 12 CT exams per subject (e.g., Mean 6.06, S.D. 2.3) were analyzed. The mean age at the time of initial CT scan was 80 years (e.g., S.D. 5.45, Range 70 to 91). The mean duration of follow up was 3.9 years (e.g., S.D. 1.75, Range 1.02 to 8.69).

TABLE 1

Distribution of MMSE scores for AD patients

| MMSE range | No. of patients |
| --- | --- |
| 10 or less | 6 |
| 11-15 | 5 |
| 16-20 | 4 |
| 21-25 | 7 |
| 26 or more | 7 |
| No MMSE available | 4 |

TABLE 2

Indications for scans[1]

| Indication | AD patients | Non-AD patients | Total |
|---|---|---|---|
| AMS | 37 | 34 | 71 |
| Fall | 30 | 37 | 67 |
| Dizziness | 19 | 24 | 43 |
| Head Trauma | 15 | 26 | 41 |
| Syncope | 19 | 18 | 37 |
| CVA evaluation | 15 | 12 | 27 |
| Headache | 13 | 14 | 27 |
| Trauma | 9 | 9 | 18 |
| ICH evaluation | 8 | 8 | 16 |
| Ataxia | 4 | 8 | 12 |
| Motor deficits | 2 | 9 | 11 |
| TIA suspect | 6 | 4 | 10 |
| Weakness | 5 | 4 | 9 |
| Focal deficit | 4 | 4 | 8 |

TABLE 2-continued

Indications for scans[1]

| Indication | AD patients | Non-AD patients | Total |
|---|---|---|---|
| Memory loss | 7 | 1 | 8 |
| CVA follow up | 3 | 2 | 5 |
| Hydrocephalus | 3 | 1 | 4 |
| HTN crisis | 2 | 1 | 3 |
| Vertigo | 1 | 2 | 3 |

[1] Since one patient can have multiple indications for a scan, and only most common indications are listed, the total number may not match the number of studies.

TABLE 3

Indications for scans for AD patients with positive acute pathology

| Indication | Total |
|---|---|
| CVA evaluation | 2 |
| Syncope | 2 |
| Dizziness | 1 |
| Fall | 1 |
| Focal deficit | 1 |
| Memory loss | 1 |
| Trauma | 1 |

TABLE 4

Indications for CT scans for non-AD patients with acute pathology [1]

| Indication | Total |
|---|---|
| Altered Mental Status | 4 |
| CVA evaluation | 2 |
| Dizziness | 2 |
| Syncope | 2 |
| Trauma | 2 |
| CVA Suspect | 1 |
| Fall | 2 |
| Focal deficit | 1 |
| Head trauma | 1 |
| Neck and back pain | 1 |
| Postoperative | 1 |
| SOL follow up | 1 |
| Weakness | 1 |

[1] One patient had two indications.

TABLE 5

Descriptive statistics by groups

| Parameter | Baseline Age (years) | | Follow up (years) | | Whole brain volume (BR'; in ml) | | Normalized whole brain volume (nBV'; as a percentage of cranial cavity) | | Brain Radiodensity (BR'; in Hounsfield units) | |
|---|---|---|---|---|---|---|---|---|---|---|
| | AD | non-AD | AD | non-AD | AD | non-AD | AD | non-AD | AD | non-AD |
| Mean | 81.08 | 79.31 | 3.95 | 3.87 | 1078.12 | 1117.06 | 80.82 | 81.81 | 30.774 | 30.484 |
| Median | 80.74 | 79.29 | 4.54 | 3.70 | 1083.00 | 1101.40 | 81.00 | 81.72 | 30.762 | 30.447 |
| Std. Dev. | 5.37 | 5.45 | 1.78 | 1.75 | 80.73 | 98.36 | 2.24 | 2.37 | 0.690 | 0.662 |
| Range | 20.37 | 19.97 | 6.21 | 7.20 | 317.73 | 399.33 | 12.48 | 15.61 | 4.373 | 4.834 |

Exemplary Test Retest Reliability Of Brain Volumetry On CT scan: ICC for ICS-V' was 0.996 with a 95% CI ranging from 0.994 to 0.997.

Exemplary Adjusted Whole Brain Volumes (Br'): FIG. 1, and Table 6 below, show changes in absolute brain volumes for AD (e.g., element 105) and non-AD patients (e.g., element 110). The model was significant for acceleration of brain volume loss in both groups (e.g., overall p-value=0.006). In non-AD group, it was 0.86 ml/yr$^2$ (e.g. 95% CI 0.64 to 1.08 ml/yr$^2$; p-value<0.001), while it was 1.32 ml/yr$^2$ (e.g. 95% CI 1.09 to 1.56 ml/yr$^2$) for AD group (e.g. intergroup p-value=0.006).

TABLE 6

Estimated rate of loss of brain volume, in milliliters and as a percentage of intracranial space

| Parameter | Estimated average slope (at individual level/Random effect) | Quadratic term (fixed effect) in ml/yr$^2$ | (95% confidence intervals) |
|---|---|---|---|
| BV', AD patients | −0.15 ml/year | −1.32 ml/yr$^2$ | (−1.56 to −1.09) |
| BV', Non-AD patients | −0.20 ml/year | −0.86 ml/yr$^2$ | (−1.08 to −0.64) |
| nBV', AD patients | −0.011%/year | −0.092%/yr$^2$ | (−0.112 to −0.072) |
| nBV', Non-AD patients | −0.016%/year | −0.058%/yr$^2$ | (−0.077 to −0.039) |

Exemplary Normalized Whole Brain Volumes (nBV'): FIG. 2 shows changes in brain volumes for AD patients (e.g., element 205) and non-AD patients (e.g., element 210) as a ratio of ICS-V'. Table 6 compares nBV' across the groups.

The model was significant for acceleration of nBV' loss for both AD and non-AD patients (e.g., overall p-value=0.017). The acceleration was 0.0578%/yr$^2$ (e.g. 95% CI 0.0389%/yr$^2$ to 0.0767%/yr$^2$; p-value<0.001) for non-AD patients. It was significantly larger, 0.0919%/yr$^2$ (e.g. 95% CI 0.0716%/yr$^2$ to 0.1122%/yr$^2$; intergroup p-value=0.017) for AD patients.

Exemplary Brain Radiodensity (BR'): FIG. 3, and Table 7 below, show changes in BR' in AD patients (e.g., element 305) and non-AD patients (e.g., element 310) over time. The model was significant for linear increase in BR' over time for non-AD patients (e.g., 0.15 Hu per year; 95% CI 0.065 Hu/year to 0.230 Hu/year; p-value=0.001). This increase in BR' did not display acceleration over time for non-AD patients (e.g., p-value for quadratic term 0.412). AD patients displayed a strong acceleration in BR' increase over time (e.g., 0.017 Hu/yr$^2$; 95% CI 0.000181 to 0.033793; p-value 0.048) without significant linear term (e.g., p-value 0.190). For the sake of consistency, the rates in FIG. 3 include both a linear and a quadratic term for both groups.

TABLE 7

Estimated annual rate of increase in brain radiodensity (in Hounsfield units)

| Group | Estimated average slope Hu/year (Random effect) | Slope as fixed effect in Hu/year | p-value | Quadratic term (fixed effect) in Hu/yr$^2$ | p-value |
|---|---|---|---|---|---|
| AD patients | −0.0029 | +0.0622 | 0.190 | +0.0169 | 0.048 |
| Non-AD patients | −0.0041 | +0.1479 | 0.001 | −0.0063 | 0.412 |

Exemplary Discussion

Exemplary Comparison With MRI: Multiple cross-sectional MRI and pathology studies suggest that brain atrophy rates accelerate after the 7th decade, even for cognitively normal individuals. (See, e.g., References 11-13). This earlier belief of accelerated atrophy can be contradicted by recent longitudinal MRI studies that found no evidence of acceleration in cognitively normal people. (See, e.g., References 14-15). Although longitudinal MRI studies consistently show that hippocampal atrophy rates do accelerate in mild cognitive impairment ("MCI") and AD patients, (see, e.g., References 14, 16) there can be conflicting evidence regarding whether or not whole brain atrophy accelerates in MCI patients or sporadic AD patients. (See, e.g., References 14 and 15). The exemplary system, method and computer-accessible medium, according to an exemplary embodiment of the present disclosure, significant quadratic terms, which can indicate acceleration of brain atrophy rates within both AD and non-AD elderly. Inter group comparison can indicate that acceleration can be significantly greater in AD patients versus non-AD patients. The exemplary results hold for both absolute brain volumes and brain volumes normalized to ICS. The rate of acceleration in brain volume loss for the patients 79 year old on average, have been reported, which can be converted from mild cognitive impairment to AD, to be 5.3 ml (e.g. 95% CI 3.3 to 7.4) over a mean duration of 4.7 years in their piecewise linear mixed model. (See, e.g., Reference 15). Their data can be in agreement with the exemplary estimate of the quadratic term (e.g., 1.32 ml/yr$^2$). It was also found that the acceleration in atrophy was 0.32%/year$^2$ in normalized whole brain volumes (e.g., 95% CI 0.15-0.50) in their cohort of familial AD. (See, e.g., Reference 6). This can be about three times larger than the exemplary estimate of 0.09%/yr$^2$ (e.g. 95% CI 0.07-0.11), which is consistent with common observation of familial AD progressing faster than sporadic AD. (See, e.g., Reference 17). Of note, CI for acceleration can be the much tighter (e.g., about ten times smaller) in the exemplary study versus previous reports, suggesting greater precision of volumetry estimated from CT than from MR images. This can be due to decreased artifact with the exemplary system, method and computer-accessible medium versus MRI resulting from faster acquisition times for the exemplary system, method and computer-accessible medium as compared to MRI.

In contrast to the information provided using the MM modality, the lower contrast present in CT images can make the image segmentation difficult for CT images. Most image processing procedures likely either under segment or over segment the image. In contrast, the exemplary system, method and computer-accessible medium, according to an exemplary embodiment of the present disclosure, can include a multi-staged process of thresholding (e.g., by selecting −500 to +125 Hu), performing morphological erosions, dilations followed by compensation for instrument miscalibration in order to overcome the problems associated with the lower contrast inherent in CT images.

Exemplary Test/Retest Reliability: The ICC for ICS-V' was found it to be 0.996, suggesting excellent agreement. Reliability of volumetry on CT scan has not been previously reported. Remarkably, the exemplary reliability matches MRI estimates, despite of the use of variable CT acquisition protocols. (See, e.g., Reference 18).

Exemplary Interpretation Of Statistical Models: The exemplary system, method and computer-accessible medium, according to an exemplary embodiment of the present disclosure, can utilize both linear and quadratic terms. The linear terms, entered as the random effect, revealed significant differences between non-AD patients versus AD patients (see, e.g., Table 6). This result can imply (i) strokes and other neurological illnesses can cause acute loss of brain tissue without any increase in long-term loss of brain parenchyma, or (ii) neurodegeneration in non-AD patients can follow predominantly linear patterns, whereas in AD, the patterns can be quadratic (e.g., accelerated changes), which can reflect progressive territory, or the spread of atrophy from medial temporal to cortical brain regions. (See, e.g., Reference 19).

Exemplary Clinical Relevance: AD and non-AD patients in the exemplary study were male military veterans. While representing a select group, they can be representative of a large segment of the population. The inclusion of confounding illnesses among the non-AD group makes the exemplary study especially relevant. (See, e.g., Reference 20). Validation of CT volumetry tool in a cohort with confounding neurological illnesses enables its use within regular day-to-day clinical practice and clinical trials.

Exemplary Changes In Brain Radiodensity: Change in brain radiodensity can be a novel potential marker of AD progression. The exemplary findings can indicate calcium deposition in the cerebral arteries (see, e.g., Reference 21) or iron deposition (see, e.g., Reference 22) in the brain parenchyma in AD patients. Since brain tissue can be denser than water, dehydration in the elderly can also potentially increase brain radiodensity. Dehydration can also be a well-known cause of reversible cognitive impairment in the elderly. (See, e.g., References 23, 24). This can raise the possibility of the use of brain radiodensity as a marker of cognitive impairment and AD, independent of atrophy.

Exemplary Summary: This exemplary CT-based longitudinal brain volumetry analysis suggests that the exemplary system, method and computer-accessible medium should be considered for monitoring the progression and treatment of AD accelerated within subject atrophy. This was shown not only for AD patients, but also for non-AD patients. Confidence intervals for the quadratic term were only within about 0.4 ml/yr$^2$ for absolute brain volumes, indicating a potential for atrophy on a CT scan to serve as a reliable outcome measure for clinical trials. The use of brain radiodensity can also serve as a new AD biomarker. This can also help shed further light on the pathology of this relentless destroyer of the brains and lives.

Figure 4A:
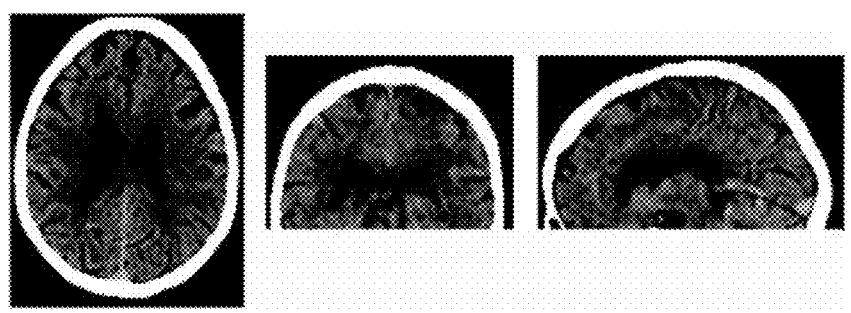
FIG. 4A is a set of exemplary images of a computed tomography head scan according to an exemplary embodiment of the present disclosure.
Figure 4B:
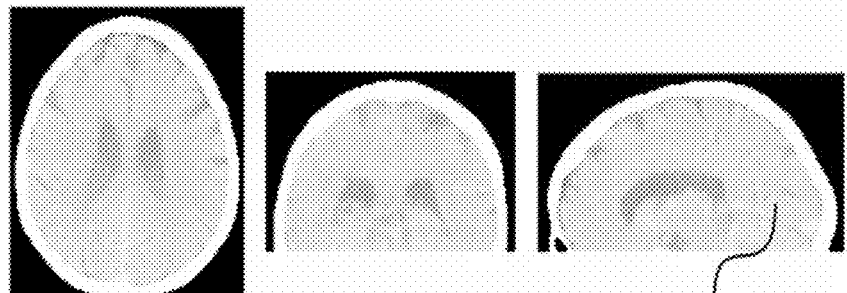
FIG. 4B is a set of exemplary images of the identification of the intracranial space (e.g., Stage I) according to an exemplary embodiment of the present disclosure.
Figure 4C:
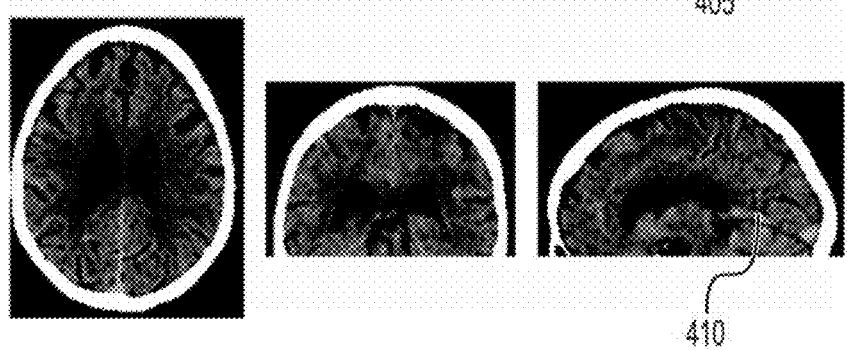
FIG. 4C is a set of exemplary images of the separation of the intracranial space (e.g., Stage II) into brain parenchyma and cerebrospinal fluid according to an exemplary embodiment of the present disclosure.

The brain atrophy and radiodensity can be estimated from CT images in two stages. (See, e.g., FIGS. 4A-4C). First, at Stage I (see, e.g., FIG. 4B), the ICS can be identified and a segmentation mask can constructed. Then intensity thresholding can be performed to separate ICS mask into brain parenchyma and CSF.

Exemplary Stage I: ICS can be identified using Edge-Wave, an exemplary procedure which can improve on a previously validated 3D segmentation tool known as Bridge Burner. The spatial resolution of CT can be approximately 0.3-0.5 mm, several times higher than for MRI. Thus, the CT dataset can include an array of 512×512×N of 16 bit integers (e.g. N is of the order of approximately 100). This can represent approximately 60 mb, an order of magnitude larger than a typical brain magnetic resonance ("MR") dataset. The atrophy procedure can include efficient processing speed. To process this exemplary dataset, a fully parallel EdgeWave procedure and computer code can be used.

To address CT segmentation, EdgeWave can begin by selecting voxels with CT attenuation of soft tissue. For a well-calibrated CT scanner, this can correspond to the range of about [−500, +125 Hu]. To eliminate small soft tissue structures like nerves or blood vessels that link the brain and the face, a 3D morphologic erosion (e.g. default radius=5 mm) can be performed. This procedure can follow the previous wave-front propagation, except that the current wave front can be grown in parallel along multiple directions.

The exemplary EdgeWave procedure can retain rich information about the wave-front, including the current wave's distance to the ancestor mask. The data addresses new applications, such as statistical description of the surface curvature, including the distribution of the heights or the depths of the mask. The temporal evolution of wave-front recorded by the exemplary EdgeWave procedure can be explored for several clinical imaging application: (i) image-based tumor characterization to stage malignancy, (ii) the analysis of brain sulci pattern to diagnose hydrocephalus, and (iii) differentiation of Alzheimer's disease from front-temporal dementia etc.

The exemplary system, method and computer-accessible medium, according to an exemplary embodiment of the present disclosure, can assure efficient processing by dispensing with the relatively slow search for a seed region (e.g., normally performed for MRI segmentation). ICC (e.g., element 405 in FIG. 4B) can be identified in a CT exam as the largest connected component of EdgeWave output. To provide flexibility in applying the exemplary procedure to other organs and structures, the following can be retained:
  i) k-th largest connected components (e.g. k can be user-defined, but k=1 can perform well for CT modality);
  ii) all connected components; and/or
  iii) connected component that contains or intersects the seed region (e.g. BridgeBurner choice).

The exemplary process can be finalized by constrained morphologic dilation. The parallel processing can be performed to take advantage of modern multi-core CPU hardware.

Figure 5:
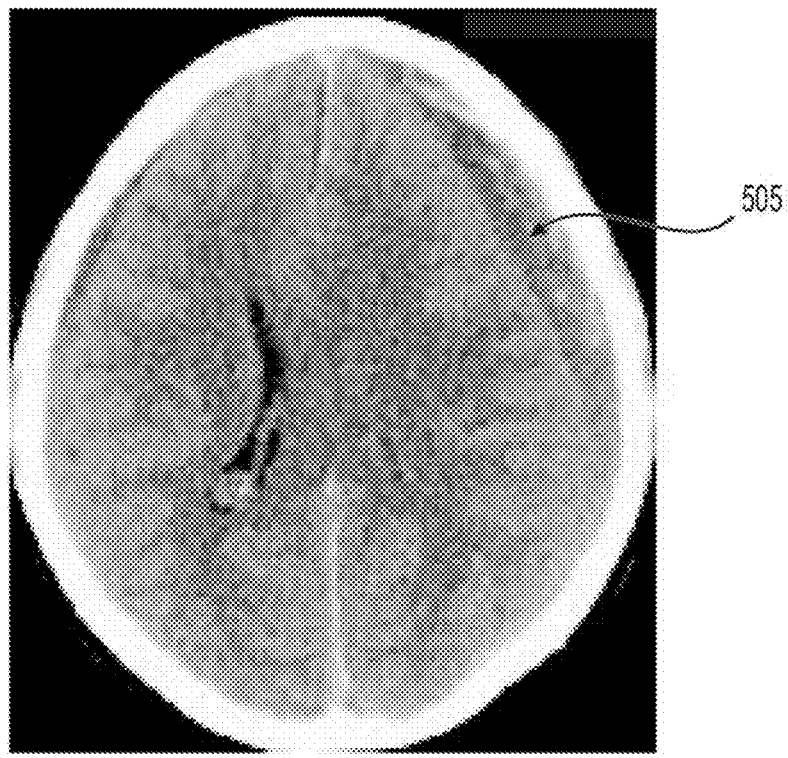
FIG. 5 is an exemplary image of a stage I intracranial space according to an exemplary embodiment of the present disclosure.

Exemplary Stage II: The ICC can be decomposed in two or more distinct tissues. For clinical applications that utilize brain atrophy estimates, ICC can be split into CSF (e.g., element 410 in FIG. 4C) and the brain. For surgical applications that optimize hematoma drainage, the goal can be to identify the area of chronic subdural hematoma. In addition to the application of brain atrophy (e.g., CSF versus the brain) CT texture can be used to identify subdural hematoma (e.g., element 505 in FIG. 5). As shown in FIG. 5, there can be a similar average intensity but a distinct texture of hematoma versus the brain.

Figure 6A:
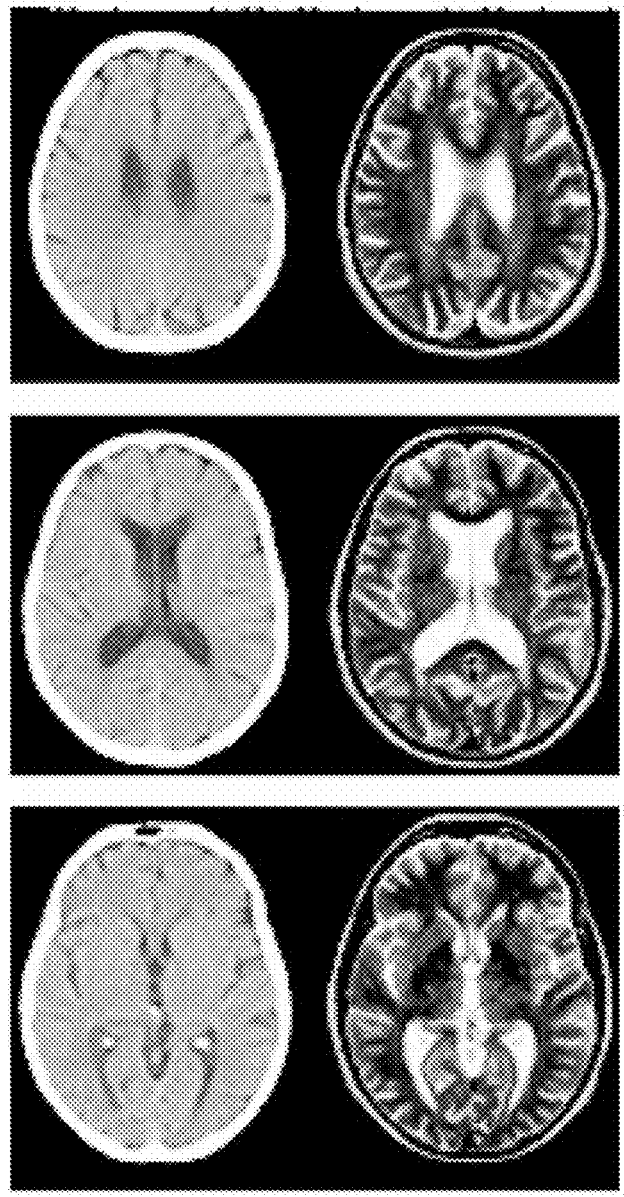
FIG. 6A is a set of exemplary images of a brain according to an exemplary embodiment of the present disclosure.

The exemplary procedure for separating CSF from the brain (see, e.g., FIGS. 6A-6C) can be based on multimodality coregistration of CT & $T_2$-weighted MM. FIG. 6A shows a set of exemplary images of a brain according to an exemplary embodiment of the present disclosure. Optimal separation of CSF (e.g. element 605 shown in FIGS. 6B and 6C) from the brain at CT can be derived by imaging individuals with both CT (see, e.g., FIG. 6B) and. $T_2$-weighted MRI (see, e.g., FIG. 6C). MRI can be used as the reference due to its superior CSF-brain contrast. The upper threshold T for CSF CT attenuation can be varied in a continuous fashion to achieve the volume ratio observed in $T_2$-weighted MRI.

Figure 12A:
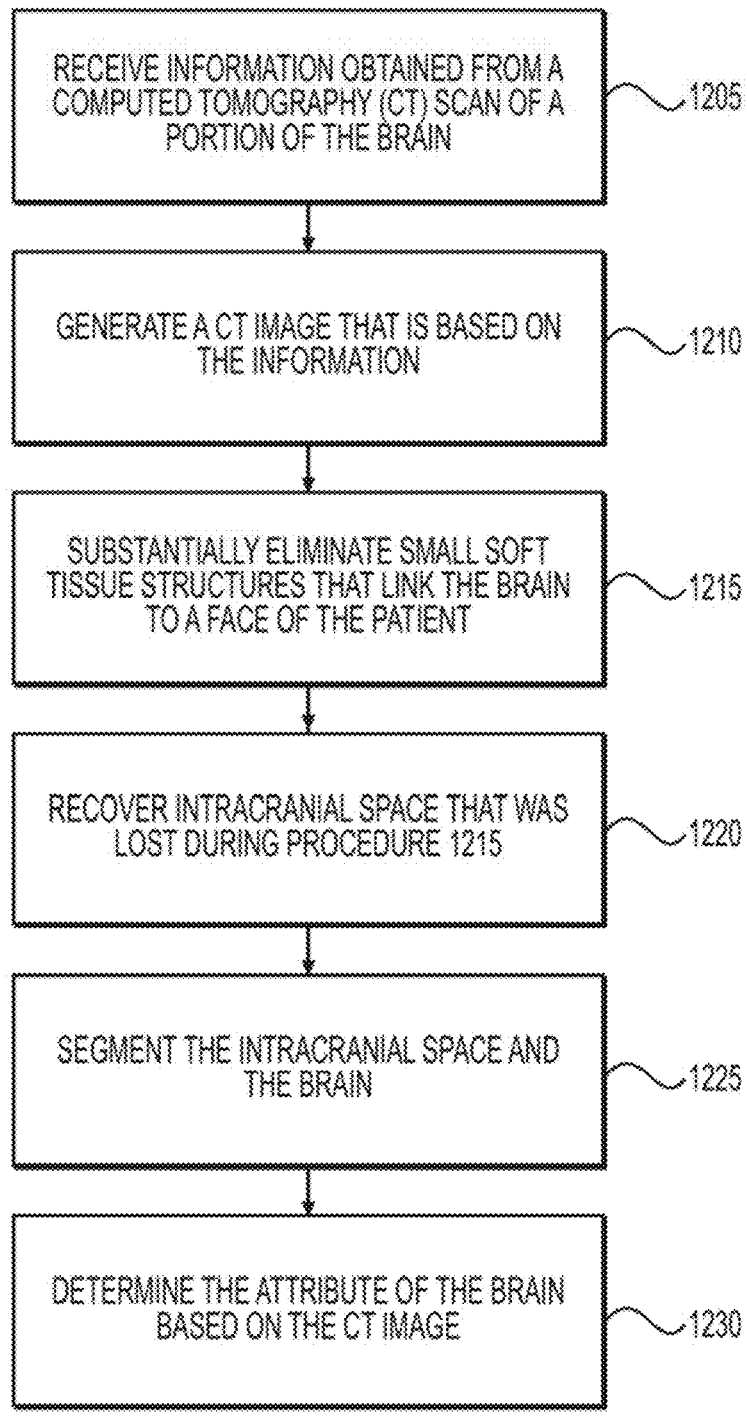
FIG. 12A is an exemplary flow diagram of an exemplary method for determining an attribute of a brain of a patient according to an exemplary embodiment of the present disclosure.

FIG. 12A shows an exemplary flow diagram of an exemplary method 1200 for determining an attribute(s) of a brain of a patient according to an exemplary embodiment of the present disclosure. For example, at procedure 1205, information obtained from a CT scan(s) of a portion(s) of the brain can be received. At procedure 1210, a CT image(s) can be generated that can be based on the information. At procedure 1215, small soft tissue structures that link the brain to a face of the patient can be substantially eliminated from the CT image(s). At procedure 1220, any ICS that was lost during the removal of the small soft tissue structures can be recovered. At procedure 1225, the intracranial space can be segmented from the brain, and at procedure 1230, the attribute(s) of the brain can be determined based on the segmented CT image(s).

Figure 12B:
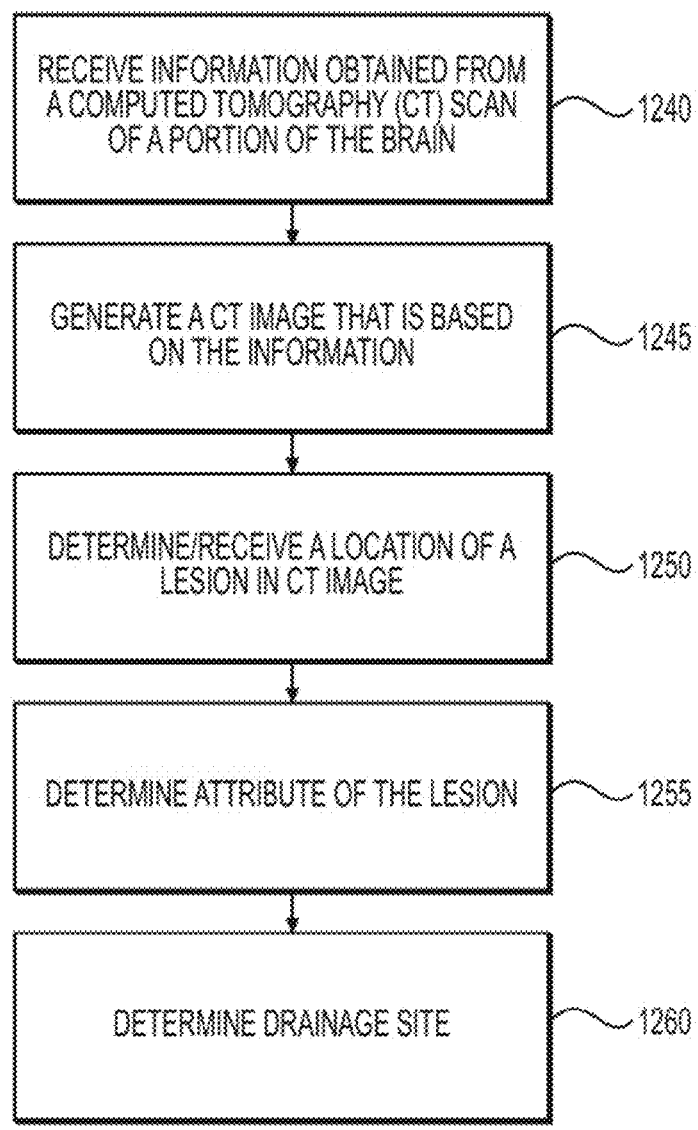
FIG. 12B is an exemplary flow diagram of an exemplary method for determining a drainage site of a lesion in a patient according to an exemplary embodiment of the present disclosure.
Figure 13:
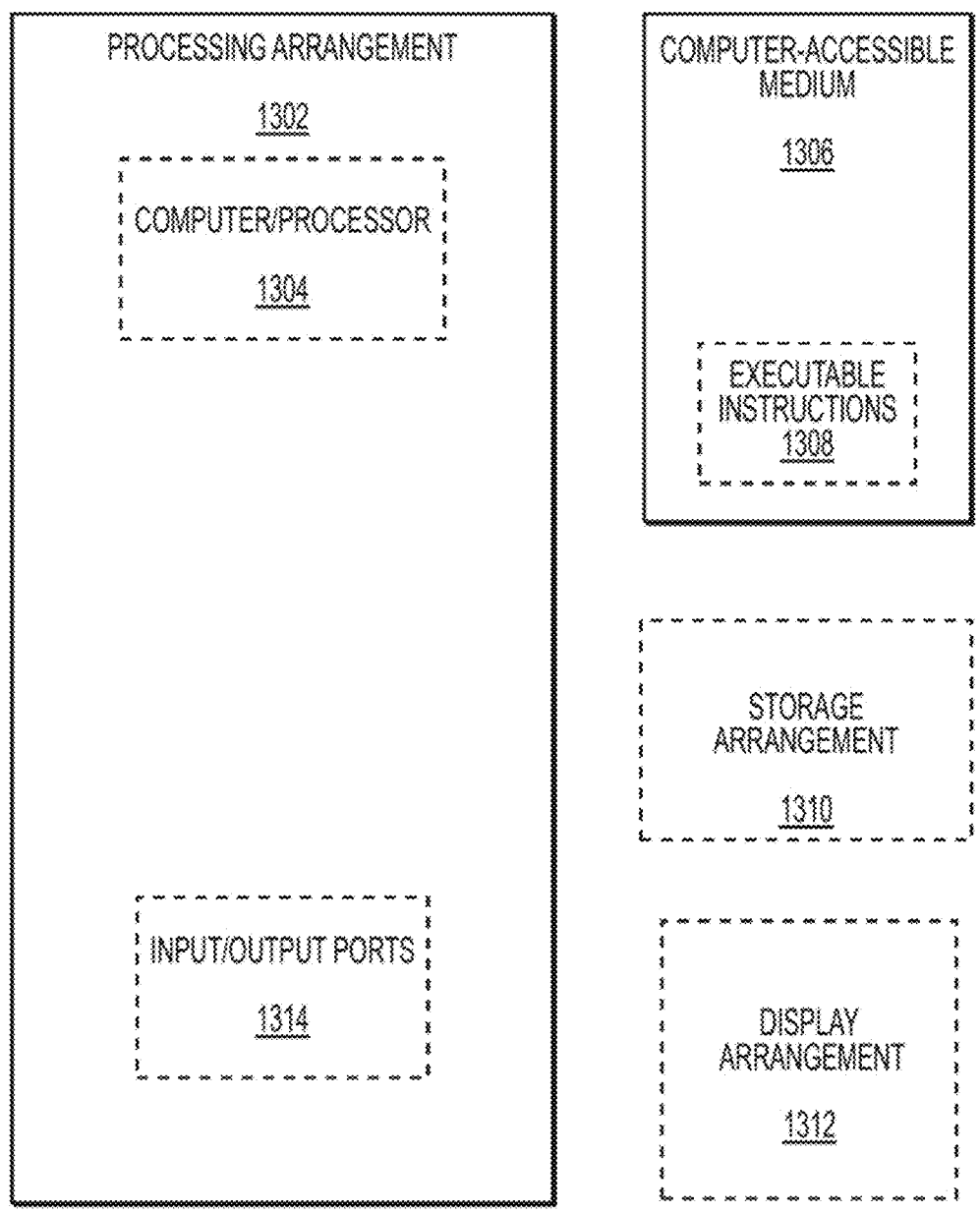
FIG. 13 is an illustration of an exemplary block diagram of an exemplary system in accordance with certain exemplary embodiments of the present disclosure.

FIG. 12B shows an exemplary flow diagram of an exemplary method 1235 for determining a drainage site of a lesion in a patient according to an exemplary embodiment of the present disclosure. For example, at procedure 1240, information obtained from a CT scan(s) the brain can be received. At procedure 1245, a CT image(s) can be generated that can be based on the information. At procedure 1250, a location of a lesion in the CT can be automatically determined by, for example, a computing arrangement (e.g., as shown in FIG. 13). Additionally, or alternatively, at procedure 1250, the location of the lesion can be determined by a person (e.g., a doctor), and the location can be transmitted to/received by the computing arrangement. At procedure 1255, an attribute of the lesion can be determined. At procedure 1260, the drainage site can be determined based on the attribute.

FIG. 13 shows a block diagram of an exemplary embodiment of a system according to the present disclosure. For example, exemplary procedures in accordance with the present disclosure described herein can be performed by a processing arrangement and/or a computing arrangement 1302. Such processing/computing arrangement 1302 can be, for example entirely or a part of, or include, but not limited to, a computer/processor 1304 that can include, for example one or more microprocessors, and use instructions stored on a computer-accessible medium (e.g., RAM, ROM, hard drive, or other storage device).

As shown in FIG. 13, for example a computer-accessible medium 1306 (e.g., as described herein above, a storage device such as a hard disk, floppy disk, memory stick, CD-ROM, RAM, ROM, etc., or a collection thereof) can be provided (e.g., in communication with the processing arrangement 1302). The computer-accessible medium 1306 can contain executable instructions 1308 thereon. In addition or alternatively, a storage arrangement 1310 can be provided separately from the computer-accessible medium 1306, which can provide the instructions to the processing arrangement 1302 so as to configure the processing arrangement to execute certain exemplary procedures, processes and methods, as described herein above, for example.

Further, the exemplary processing arrangement 1302 can be provided with or include an input/output arrangement 1314, which can include, for example a wired network, a wireless network, the internet, an intranet, a data collection probe, a sensor, etc. As shown in FIG. 13, the exemplary processing arrangement 1302 can be in communication with an exemplary display arrangement 1312, which, according to certain exemplary embodiments of the present disclosure, can be a touch-screen configured for inputting information to the processing arrangement in addition to outputting information from the processing arrangement, for example. Further, the exemplary display 1312 and/or a storage arrangement 1310 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

1. de Leon M J, George A E, Stylopoulos L A, Smith G, Miller D C. Early marker for Alzheimer's disease: the atrophic hippocampus. Lancet. 1989; 2(8664):672-3.
2. Jack C R, Jr., Shiung M M, Gunter J L, O'Brien P C, Weigand S D, Knopman D S, et al. Comparison of different MRI brain atrophy rate measures with clinical disease progression in AD. Neurology. 2004; 62(4):591-600.
3. Resnick S M, Pham D L, Kraut M A, Zonderman A B, Davatzikos C. Longitudinal magnetic resonance imaging studies of older adults: a shrinking brain. J Neurosci. 2003; 23(8):3295-301.
4. Thompson P M, Hayashi K M, de Zubicaray G, Janke A L, Rose S E, Semple J, et al. Dynamics of gray matter loss in Alzheimer's disease. J Neurosci. 2003; 23(3):994-1005.
5. Wang D, Doddrell D M. MR image-based measurement of rates of change in volumes of brain structures. Part I: method and validation. Magnetic resonance imaging. 2002; 20(1):27-40.
6. Chan D, Janssen J C, Whitwell J L, Watt H C, Jenkins R, Frost C, et al. Change in rates of cerebral atrophy over time in early-onset Alzheimer's disease: longitudinal MRI study. Lancet. 2003; 362(9390):1121-2.
7. Frank R A, Galasko D, Hampel H, Hardy J, de Leon M J, Mehta P D, et al. Biological markers for therapeutic trials in Alzheimer's disease. Proceedings of the biological markers working group; NIA initiative on neuroimaging in Alzheimer's disease. Neurobiology of aging. 2003; 24(4):521-36.
8. Gunter J L, Shiung M M, Manduca A, Jack C R, Jr. Methodological considerations for measuring rates of brain atrophy. Journal of magnetic resonance imaging: JMRI. 2003; 18(1):16-24.
9. Mikheev A, Nevsky G, Govindan S, Grossman R, Rusinek H. Fully automatic segmentation of the brain from T1-weighted MRI using Bridge Burner algorithm. Journal of magnetic resonance imaging: JMRI. 2008; 27(6):1235-41.
10. Bin Zahid A, Mikheev A, Yang A I, Samadani U, Rusinek H, editors. Calculation of brain atrophy using computed tomography and a new atrophy measurement tool. Proc *SPIE* 9413, Medical Imaging 2015: Image Processing, 94132S; 2015 Feb. 21; Orlando, Fla.
11. Dekaban A S. Changes in brain weights during the span of human life: relation of brain weights to body heights and body weights. Ann Neurol. 1978; 4(4):345-56.
12. Scahill R I, Frost C, Jenkins R, Whitwell J L, Rossor M N, Fox N C. A longitudinal study of brain volume changes in normal aging using serial registered magnetic resonance imaging. Arch Neurol. 2003; 60(7):989-94.
13. Courchesne E, Chisum H J, Townsend J, Cowles A, Covington J, Egaas B, et al. Normal brain development and aging: quantitative analysis at in vivo MR imaging in healthy volunteers. Radiology. 2000; 216(3):672-82.
14. Leung K K, Bartlett J W, Barnes J, Manning E N, Ourselin S, Fox N C, et al. Cerebral atrophy in mild cognitive impairment and Alzheimer disease: rates and acceleration. Neurology. 2013; 80(7):648-54.
15. Jack C R, Jr., Weigand S D, Shiung M M, Przybelski S A, O'Brien P C, Gunter J L, et al. Atrophy rates accelerate in amnestic mild cognitive impairment. Neurology. 2008; 70(19 Pt 2):1740-52.
16. Schuff N, Woerner N, Boreta L, Kornfield T, Shaw L M, Trojanowski J Q, et al. MRI of hippocampal volume loss in early Alzheimer's disease in relation to ApoE genotype and biomarkers. Brain: a journal of neurology. 2009; 132(Pt 4):1067-77.
17. Swearer J M, O'Donnell B F, Ingram S M, Drachman D A. Rate of progression in familial Alzheimer's disease. J Geriatr Psychiatry Neurol. 1996; 9(1):22-5.

18. Nugent A C, Luckenbaugh D A, Wood S E, Bogers W, Zarate C A, Jr., Drevets W C. Automated subcortical segmentation using FIRST: test-retest reliability, inter-scanner reliability, and comparison to manual segmentation. Human brain mapping. 2013; 34(9):2313-29.
19. Rusinek H, Endo Y, De Santi S, Frid D, Tsui W H, Segal S, et al. Atrophy rate in medial temporal lobe during progression of Alzheimer disease. Neurology. 2004; 63(12):2354-9.
20. Ganguli M, Lee C W, Hughes T, Snitz B E, Jakubcak J, Duara R, et al. Who wants a free brain scan? Assessing and correcting for recruitment biases in a population-based sMRI pilot study. Brain Imaging Behav. 2015; 9(2):204-12.
21. Bos D, Ikram M A, Elias-Smale S E, Krestin G P, Hofman A, Witteman J C, et al. Calcification in major vessel beds relates to vascular brain disease. Arteriosclerosis, thrombosis, and vascular biology. 2011; 31(10): 2331-7.
22. Kirsch W, McAuley G, Holshouser B, Petersen F, Ayaz M, Vinters H V, et al. Serial susceptibility weighted MRI measures brain iron and microbleeds in dementia. Journal of Alzheimer's disease: JAD. 2009; 17(3):599-609.
23. Kempton M J, Ettinger U, Foster R, Williams S C, Calvert G A, Hampshire A, et al. Dehydration affects brain structure and function in healthy adolescents. Human brain mapping. 2011; 32(1):71-9.
24. Duning T, Kloska S, Steinstrater O, Kugel H, Heindel W, Knecht S. Dehydration confounds the assessment of brain atrophy. Neurology. 2005; 64(3):548-50.
25. Balser D, Farooq S, Mehmood T, Reyes M, Samadani U. Actual and projected incidence rates for chronic subdural hematomas in United States Veterans Administration and civilian populations. J Neurosurg 2015:1-7.
26. Miranda L B, Braxton E, Hobbs J, Quigley M R. Chronic subdural hematoma in the elderly: not a benign disease. Journal of neurosurgery 2011; 114:72-6.
27. Frati A, Salvati M, Mainiero F, et al. Inflammation markers and risk factors for recurrence in 35 patients with a posttraumatic chronic subdural hematoma: a prospective study. J Neurosurg 2004; 100:24-32.
28. Ohba S, Kinoshita Y, Nakagawa T, Murakami H. The risk factors for recurrence of chronic subdural hematoma. Neurosurgical review 2013; 36:145-9; discussion 9-50.
29. Almenawer S A, Farrokhyar F, Hong C, et al. Chronic subdural hematoma management: a systematic review and meta-analysis of 34,829 patients. Annals of surgery 2014; 259:449-57.
30. Liu W, Bakker N A, Groen R J. Chronic subdural hematoma: a systematic review and meta-analysis of surgical procedures. J Neurosurg 2014; 121:665-73.
31. Balser D, Rodgers S D, Johnson B, Shi C, Tabak E, Samadani U. Evolving management of symptomatic chronic subdural hematoma: experience of a single institution and review of the literature. Neurol Res 2013; 35:233-42.
32. Safain M, Roguski M, Antoniou A, Schirmer C M, Malek A M, Riesenburger R. A single center's experience with the bedside subdural evacuating port system: a useful alternative to traditional methods for chronic subdural hematoma evacuation. J Neurosurg 2013; 118:694-700.
33. Altamura S, Muckenthaler M U. Iron toxicity in diseases of aging: Alzheimer's disease, Parkinson's disease and atherosclerosis. Journal of Alzheimer's disease: JAD 2009; 16:879-95.
34. Hua Y, Keep R F, Hoff J T, Xi G. Brain injury after intracerebral hemorrhage: the role of thrombin and iron. Stroke 2007; 38:759-62.
35. Mills E, Dong X P, Wang F, Xu H. Mechanisms of brain iron transport: insight into neurodegeneration and CNS disorders. Future medicinal chemistry 2010; 2:51-64.
36. Xi G, Keep R F, Hoff J T. Mechanisms of brain injury after intracerebral haemorrhage. The Lancet Neurology 2006; 5:53-63.
37. Dumont T M, Rughani A I, Goeckes T, Tranmer B I. Chronic subdural hematoma: a sentinel health event. World neurosurgery 2013; 80:889-92.
38. Nagata K, Asano T, Basugi N, Tango T, Takakura K. [Studies on the operative factors affecting the reduction of chronic subdural hematoma, with special reference to the residual air in the hematoma cavity]. No shinkei geka 1989; 17:15-20.
39. Nakaguchi H, Tanishima T, Yoshimasu N. Relationship between drainage catheter location and postoperative recurrence of chronic subdural hematoma after burr-hole irrigation and closed-system drainage. J Neurosurg 2000; 93:791-5.
40. Leroy H A, Aboukais R, Reyns N, et al. Predictors of functional outcomes and recurrence of chronic subdural hematomas. Journal of clinical neuroscience: official journal of the Neurosurgical Society of Australasia 2015; 22:1895-900.
41. Lega B C, Danish S F, Malhotra N R, Sonnad S S, Stein S C. Choosing the best operation for chronic subdural hematoma: a decision analysis. J Neurosurg 2010; 113: 615-21.
42. Neils D M, Singanallur P S, Wang H, et al. Recurrence-Free Chronic Subdural Hematomas: A Retrospective Analysis of the Instillation of Tissue Plasminogen Activator in Addition to Twist Drill or Burr Hole Drainage in the Treatment of Chronic Subdural Hematomas. World neurosurgery: 2012 Elsevier Inc; 2011.
43. Cenic A, Bhandari M, Reddy K. Management of chronic subdural hematoma: a national survey and literature review. The Canadian journal of neurological sciences Le journal canadien des sciences neurologiques 2005; 32:501-6.
44. Ducruet A F, Grobelny B T, Zacharia B E, et al. The surgical management of chronic subdural hematoma. Neurosurgical review 2012; 35:155-69; discussion 69.
45. Hamilton M G, Frizzell J B, Tranmer B I. Chronic subdural hematoma: the role for craniotomy reevaluated. Neurosurgery 1993; 33:67-72.
46. Kudo H, Kuwamura K, Izawa I, Sawa H, Tamaki N. Chronic subdural hematoma in elderly people: present status on Awaji Island and epidemiological prospect. Neurologia medico-chirurgica 1992; 32:207-9.
47. Filippini G. Epidemiology of primary central nervous system tumors. Handb Clin Neurol 2012; 104:3-22.
48. Gavrilovic I T, Posner J B. Brain metastases: epidemiology and pathophysiology. J Neurooncol 2005; 75:5-14.
49. Bray R M, Pemberton M R, Hourani L L, Witt M, Olmsted K L R, Brown J M. 2008 Department of Defense survey of health related behaviors among active duty military personnel. RTI International 2009.
50. Bohnert A S, Ilgen M A, Bossarte R M, Britton P C, Chermack S T, Blow F C. Veteran status and alcohol use in men in the United States. Military medicine 2012; 177:198-203.

51. Mellergard P, Wisten O. Operations and re-operations for chronic subdural haematomas during a 25-year period in a well defined population. Acta Neurochir (Wien) 1996; 138:708-13.
52. Gelabert-Gonzalez M, Iglesias-Pais M, Garcia-Allut A, Martinez-Rumbo R. Chronic subdural haematoma: surgical treatment and outcome in 1000 cases. Clin Neurol Neurosurg 2005; 107:223-9.
53. Markwalder T-M. Chronic subdural hematomas: a review. Journal of neurosurgery 1981; 54:637-45.
54. Hoge C W, McGurk D, Thomas J L, Cox A L, Engel C C, Castro C A. Mild traumatic brain injury in US soldiers returning from Iraq. New England Journal of Medicine 2008; 358:453-63.
55. Lee K S. The pathogenesis and clinical significance of traumatic subdural hygroma. Brain injury: [BI] 1998; 12:595-603.
56. Cole J H, Leech R, Sharp D J. Prediction of brain age suggests accelerated atrophy after traumatic brain injury. Annals of neurology 2015; 77:571-81.
57. Frontera J A, de los Reyes K, Gordon E, et al. Trend in outcome and financial impact of subdural hemorrhage. Neurocritical care 2011; 14:260-6.
58. Taber K H, Warden D L, Hurley R A. Blast-related traumatic brain injury: what is known? 2014.
59. Suzuki K, Takano S, Nose T, Doi M, Ohashi N. Increased concentration of vascular endothelial growth factor (VEGF) in chronic subdural hematoma. J Trauma 1999; 46:532-3.
60. Weigel R, Schmiedek P, Krauss J. Outcome of contemporary surgery for chronic subdural haematoma: evidence based review. Journal of Neurology, Neurosurgery & Psychiatry 2003; 74:937-43.
61. Weigel R, Schilling L, Schmiedek P. Specific pattern of growth factor distribution in chronic subdural hematoma (CSH): evidence for an angiogenic disease. Acta neurochirurgica 2001; 143:811-8; discussion 9.
62. Ito H, Komai T, Yamamoto S. Fibrin and fibrinogen degradation products in chronic subdural hematoma. Neurologia medico-chirurgica 1975; 15 pt 1:51-5.
63. De Jesus O, Pacheco H, Negron B. Chronic and subacute subdural hematoma in the adult population. The Puerto Rico experience. PR Health Sci J 1998; 17:227-33.
64. Iantosca M R, Simon R H. Chronic subdural hematoma in adult and elderly patients. Neurosurg Clin N Am 2000; 11:447-54.
65. Goksu E, Akyuz M, Ucar T, Kazan S. Spontaneous resolution of a large chronic subdural hematoma: a case report and review of the literature. Ulusal travma ye acil cerrahi dergisi=Turkish journal of trauma & emergency surgery: TJTES 2009; 15:95-8.
66. Juković M, Kojadinović , Till V. Complete spontaneous resolution of compressive chronic subdural hematoma in a patient with liver failure. Kompletna spontana resorpcij a kompresivnog hroničnog subduralnog hematoma kod pacijentkinje s oštećenjem jetre 2012; 9:417-20.
67. Sarnvivad P, Chiewchanvechakul W, Chumnanvej S. Chronic subdural hematoma: drainage vs. no drainage. Journal of the Medical Association of Thailand=Chotmaihet thangphaet 2011; 94:1352-6.
68. Gokmen M, Sucu H K, Ergin A, Gokmen A, Bezircio Lu H. Randomized comparative study of burr-hole craniostomy versus twist drill craniostomy; surgical management of unilateral hemispheric chronic subdural hematomas. Zentralblatt fur Neurochirurgie 2008; 69:129-33.
69. Santarius T, Lawton R, Kirkpatrick P J, Hutchinson P J. The management of primary chronic subdural haematoma: a questionnaire survey of practice in the United Kingdom and the Republic of Ireland. Br J Neurosurg. England2008:529-34.
70. Borger V, Vatter H, Oszvald A, Marquardt G, Seifert V, Guresir E. Chronic subdural haematoma in elderly patients: a retrospective analysis of 322 patients between the ages of 65-94 years. Acta neurochirurgica 2012.
71. Nayil K, Ramzan A, Saj ad A, et al. Subdural hematomas: an analysis of 1181 Kashmiri patients. World neurosurgery. United States: A 2012 Elsevier Inc; 2012:103-10.
72. Kolias A G, Sinha R, Park H, Santarius T, Hutchinson P J. Surgical management of chronic subdural hematomas: in need of better evidence. Acta neurochirurgica 2013; 155:183-4.
73. Mori K, Maeda M. Surgical treatment of chronic subdural hematoma in 500 consecutive cases: clinical characteristics, surgical outcome, complications, and recurrence rate. Neurologia medico-chirurgica 2001; 41:371-81.
74. Tahsim-Oglou Y, Beseoglu K, Hanggi D, Stummer W, Steiger H J. Factors predicting recurrence of chronic subdural haematoma: the influence of intraoperative irrigation and low-molecular-weight heparin thromboprophylaxis. Acta neurochirurgica 2012; 154:1063-7; discussion 8.
75. Berhouma M, Jacquesson T, Jouanneau E. The minimally invasive endoscopic management of septated chronic subdural hematomas: surgical technique. Acta neurochirurgica 2014; 156:2359-62.
76. Shimizu S, Mochizuki T, Osawa S, Kumabe T. Intraoperative Ultrasonography during Drainage for Chronic Subdural Hematomas: A Technique to Release Isolated Deep-seated Hematomas-Technical Note. Neurologia medico-chirurgica 2015; 55:761-5.
77. Yang A I, Balser D S, Mikheev A, et al. Cerebral atrophy is associated with development of chronic subdural haematoma. Brain Inj 2012.
78. Kenning T J, Dalfino J C, German J W, Drazin D, Adamo M A. Analysis of the subdural evacuating port system for the treatment of subacute and chronic subdural hematomas. J Neurosurg 2010; 113:1004-10.
79. Neal M T, Hsu W, Urban J E, Angelo N M, Sweasey T A, Branch C L, Jr. The subdural evacuation port system: outcomes from a single institution experience and predictors of success. Clin Neurol Neurosurg 2013; 115:658-64.
80. McKhann G M, Knopman D S, Chertkow H, et al. The diagnosis of dementia due to Alzheimer's disease: recommendations from the National Institute on Aging-Alzheimer's Association workgroups on diagnostic guidelines for Alzheimer's disease. Alzheimers Dement 2011; 7:263-9.
81. Beer F P, Johnston Jr E R, Cornwell P J. Chapter 9: Determination of the principal axes of a body of arbitrary shape. Vector mechanics for engineers: Dynamics. 9th ed. Boston: McGraw-Hill; 2010.

What is claimed is:
1. A non-transitory computer-accessible medium having stored thereon computer-executable instructions for determining at least one attribute of a brain of a patient, wherein, when a computer arrangement executes the instructions, the computer arrangement is configured to perform procedures comprising:
receiving information obtained from at least one computed tomography (CT) scan of at least one portion of the intracranial cavity;

generating at least one CT image based on the information; and determining the at least one attribute of the area(s) of interest identified based on the at least one CT image by segmenting an intracranial space (ICS) in the at least one CT image.

2. The computer-accessible medium of claim 1, wherein the at least one attribute includes at least one of (i) a brain volume, (ii) a cerebral spinal fluid volume, (iii) a presence or absence of Alzheimer's disease, (iv) vascular dementia, (v) normal pressure hydrocephalus, (vi) post traumatic dementia, (vii) post infectious atrophy, (viii) Creutzfeld-Jacob, (ix) a total volume of the brain or brain volume as a percentage of cranial cavity, or (x) volume of the CSF or volume of the CSF as a percentage of cranial cavity or volume of the lesion or volume of the lesion as a percentage of other structure(s).

3. The computer-accessible medium of claim 1, wherein the computer arrangement segments the ICS using an Edge-Wave procedure.

4. The computer-accessible medium of claim 3, wherein the EdgeWave procedure is a parallel procedure.

5. The computer-accessible medium of claim 3, wherein the computer arrangement performs the EdgeWave procedure by selecting a plurality of voxels in the second imaging information that have a particular CT attenuation range.

6. The computer-accessible medium of claim 5, wherein the particular attenuation range is from about −500 Hounsfield units (HU) to about +125 HU.

7. The computer-accessible medium of claim 3, wherein the computer arrangement is further configured to eliminate, from the at least one CT image, small soft tissue structures that link the intracranial cavity to the extracranial soft tissues.

8. The computer-accessible medium of claim 7, wherein the computer arrangement eliminates the small soft tissue structures using a morphological erosion procedure.

9. The computer-accessible medium of claim 8, wherein a default radius of the morphological erosion procedure is about 5 millimeters.

10. The computer-accessible medium of claim 7, wherein the small soft tissue structures include nerves and blood vessels.

11. The computer-accessible medium of claim 3, wherein the computer arrangement is further configure to determine the ICS based on the at least one CT image.

12. The computer-accessible medium of claim 11, wherein the computer arrangement is further configured to decompose the ICS into at least two distinct portions.

13. The computer-accessible medium of claim 12, wherein the at least two distinct portions include cerebral spinal fluid (CSF) volume and/or brain of the patient and the brain.

14. The computer-accessible medium of claim 13, wherein the computer arrangement decomposes the ICC by separating the CSF volume from the brain by selecting all ICS voxels having an attenuation value with a fluid range.

15. The computer-accessible medium of claim 14, wherein the fluid range is at least one of (i) less than about 25 Hounsfield units, or (ii) based on a visual inspection of the CT image by at least one person.

16. The computer-accessible medium of claim 14, wherein the computer arrangement separates the CSF volume from the brain using a multimodality co-registration procedure, or visual inspection.

17. The computer-accessible medium of claim 16, wherein the multimodality co-registration procedure is based on CT and $T_2$-weighted magnetic resonance imaging.

18. A method for determining at least one attribute of a brain of a patient, comprising:
receiving information comprising at least one computed tomography (CT) scan of the brain;
generating at least one CT image based on the imaging information; and
using a computer hardware arrangement, determining the at least one attribute of the brain based on the at least one CT image by segmenting intracranial space (ICS) in the at least one CT image.

19. A system for determining at least one attribute of a brain of a patient, comprising:
using a computer hardware arrangement, receiving information obtained from at least one computed tomography (CT) scan of the brain;
generating at least one CT image based on the information; and
determining the at least one attribute of the brain based on the at least one CT image.

20. A non-transitory computer-accessible medium having stored thereon computer-executable instructions for determining a drainage site of at least one lesion in a patient, wherein, when a computer arrangement executes the instructions, the computer arrangement is configured to perform procedures comprising:
receiving a location of the at least one lesion in at least one computed tomography (CT) image;
determining at least one attribute of the at least one lesion; and
determining the drainage site based on the at least one attribute.

21. The computer-accessible medium of claim 20, wherein the at least one attribute includes at least one of (i) a centroid, (ii) a density weighted centroid, (iii) a major axis, (iv) a minor axis, (v) a topmost part of the at least one lesion or (vi) a most dependent part of the subdural hematoma.

22. The computer-accessible medium of claim 20, wherein the computer arrangement determines the at least one attribute based on at least one of (i) a shape of the at least one lesion, (ii) a type of the at least one lesion or (iii) a septation of the at least one lesion.

23. The computer-accessible medium of claim 20, wherein the at least one lesion is at least one of (i) a hematoma, (ii) a subdural hygroma, (iii) an abscess on a surface of a brain of the patient or (iv) a solid that has aspirated through a drain of the patient.

24. The computer-accessible medium of claim 20, wherein the drainage site is at least one of (i) a point on a scale that is determined based on the at least one attribute, or (ii) an optimal drainage site.

25. The computer-accessible medium of claim 20, wherein the location is identified by at least one person.

26. The computer-accessible medium of claim 20, wherein the computer arrangement is further configured to at least one of (i) determine the location of the at least one lesion the CT image, or (ii): receive information obtained from at least one CT scan of the at least one lesion and generate the at least one CT image based on the information.

27. A method for determining a drainage site of at least one lesion in a patient, comprising:
receiving a location of the at least one lesion in at least one computed tomography (CT) image;
determining at least one attribute of the at least one lesion; and using a computer hardware arrangement, determining the drainage site based on the at least one attribute.

28. A system for determining a drainage site of at least one lesion in a patient, comprising:

a computer hardware arrangement configured to:

receive a location of the at least one lesion in at least one computed tomography (CT) image;

determine at least one attribute of the at least one lesion; and determine the drainage site based on the at least one attribute.

* * * * *